US010455836B2

(12) United States Patent
Satchivi et al.

(10) Patent No.: US 10,455,836 B2
(45) Date of Patent: Oct. 29, 2019

(54) SYNERGISTIC WEED CONTROL FROM APPLICATIONS OF PYRIDINE CARBOXYLIC ACID HERBICIDES AND PHOTOSYSTEM II INHIBITORS

(71) Applicant: Dow AgroSciences, LLC, Indianapolis, IN (US)

(72) Inventors: Norbert M. Satchivi, Carmel, IN (US); Bryston L. Bangel, Camby, IN (US); Paul R. Schmitzer, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/854,397

(22) Filed: Sep. 15, 2015

(65) Prior Publication Data
US 2016/0135456 A1 May 19, 2016

Related U.S. Application Data

(60) Provisional application No. 62/050,712, filed on Sep. 15, 2014.

(51) Int. Cl.
A01N 43/40 (2006.01)
A01N 37/18 (2006.01)
A01N 37/34 (2006.01)
A01N 43/707 (2006.01)
A01N 43/88 (2006.01)

(52) U.S. Cl.
CPC ............ A01N 43/40 (2013.01); A01N 37/18 (2013.01); A01N 37/34 (2013.01); A01N 43/707 (2013.01); A01N 43/88 (2013.01)

(58) Field of Classification Search
CPC combination set(s) only.
See application file for complete search history.

(56) References Cited

U.S. PATENT DOCUMENTS

| 6,297,197 | B1 | 10/2001 | Fields et al. |
| 6,784,137 | B2 | 8/2004 | Balko et al. |
| 7,300,907 | B2 | 11/2007 | Epp et al. |
| 7,314,849 | B2 | 1/2008 | Balko et al. |
| 7,498,468 | B2 | 3/2009 | Balko et al. |
| 7,538,214 | B2 | 5/2009 | Epp et al. |
| 7,642,220 | B2 | 1/2010 | Epp et al. |
| 7,863,220 | B2 | 1/2011 | Clark et al. |
| 7,888,287 | B2 | 2/2011 | Epp et al. |
| 8,288,318 | B2 | 10/2012 | Epp et al. |
| 8,426,591 | B2 | 4/2013 | Guenthenspberger et al. |
| 8,536,331 | B2 | 9/2013 | Eckelbarger et al. |
| 8,609,592 | B2 | 12/2013 | Guenthenspberger et al. |
| 8,754,229 | B2 | 6/2014 | Epp et al. |
| 9,113,629 | B2 | 8/2015 | Eckelbarger et al. |
| 9,179,676 | B2 * | 11/2015 | Hoffmann ............ C07D 417/04 |
| 9,521,847 | B2 | 12/2016 | Juras et al. |
| 10,231,451 | B2 * | 3/2019 | Satchivi ............... C07D 405/04 |
| 2003/0114311 | A1 | 6/2003 | Balko et al. |
| 2007/0179059 | A1 | 8/2007 | Epp et al. |
| 2008/0045734 | A1 | 2/2008 | Balko et al. |
| 2008/0234262 | A1 | 9/2008 | Zask et al. |
| 2009/0048109 | A1 | 2/2009 | Epp et al. |
| 2009/0062121 | A1 | 3/2009 | Satchivi et al. |
| 2009/0088322 | A1 | 4/2009 | Epp et al. |
| 2009/0264429 | A1 | 10/2009 | Apodaca et al. |
| 2010/0137137 | A1 | 6/2010 | Rosinger et al. |
| 2010/0137138 | A1 | 6/2010 | Rosinger et al. |
| 2010/0179127 | A1 | 7/2010 | Floersheim et al. |
| 2010/0285959 | A1 | 11/2010 | Armel et al. |
| 2011/0105325 | A1 | 5/2011 | Satchivi et al. |
| 2011/0136666 | A1 * | 6/2011 | Whittingham ......... A01N 43/54 504/103 |
| 2011/0281873 | A1 | 11/2011 | Chiang et al. |
| 2012/0015811 | A1 | 1/2012 | Dave et al. |
| 2012/0115724 | A1 | 5/2012 | Whittingham et al. |

(Continued)

FOREIGN PATENT DOCUMENTS

| CA | 2842830 A1 | 1/2013 |
| WO | 2003011853 A1 | 2/2003 |

(Continued)

OTHER PUBLICATIONS

International Search Report and Written Opinion, issued in International Application No. PCT/US15/50203 dated Jan. 14, 2016.
International Search Report and Written Opinion, issued in International Application No. PCT/US15/50205 dated Jan. 14, 2016.
International Search Report and Written Opinion, issued in International Application No. PCT/US15/50209 dated Jan. 14, 2016.
International Search Report and Written Opinion of the EP International Searching Authority from International Application No. PCT/EP2012/064519 dated Sep. 28, 2012.
International Search Report and Written Opinion issued in International Application No. PCT/US2014/024745 dated Jul. 7, 2014.

(Continued)

Primary Examiner — John Pak
(74) Attorney, Agent, or Firm — Meunier Carlin & Curfman, LLC

(57) ABSTRACT

Disclosed herein are herbicidal compositions comprising a herbicidally effective amount of (a) a pyridine carboxylic acid herbicide or an agriculturally acceptable N-oxide, salt, or ester thereof, and (b) a photosystem II inhibitor, or an agriculturally acceptable salt or ester thereof. Also disclosed herein are methods of controlling undesirable vegetation which comprise applying to vegetation or an area adjacent the vegetation or applying to soil or water to prevent the emergence or growth of vegetation (a) a pyridine carboxylic acid herbicide or an agriculturally acceptable N-oxide, salt, or ester thereof, and (b) a photosystem II inhibitor, or an agriculturally acceptable salt or ester thereof, wherein (a) and (b) are each added in an amount sufficient to provide a herbicidal effect.

22 Claims, No Drawings

(56) References Cited

U.S. PATENT DOCUMENTS

| | | |
|---|---|---|
| 2012/0157314 A1 | 6/2012 | Ahrens et al. |
| 2012/0184435 A1 | 7/2012 | Bristow et al. |
| 2012/0190548 A1 | 7/2012 | Eckelbarger et al. |
| 2012/0190549 A1 | 7/2012 | Eckelbarger et al. |
| 2012/0288492 A1 | 11/2012 | Kuo et al. |
| 2012/0292905 A1 | 11/2012 | Slot |
| 2013/0310358 A1 | 11/2013 | Coats et al. |
| 2013/0345240 A1 | 12/2013 | Whitten et al. |
| 2014/0031215 A1 | 1/2014 | Yerkes et al. |
| 2014/0031222 A1 | 1/2014 | Yerkes et al. |
| 2014/0274695 A1 | 9/2014 | Eckelbarger et al. |
| 2014/0274701 A1 | 9/2014 | Eckelbarger et al. |
| 2015/0005165 A1 | 1/2015 | Hoffmann et al. |

FOREIGN PATENT DOCUMENTS

| | | |
|---|---|---|
| WO | 2005063721 A1 | 7/2005 |
| WO | 2006121648 A2 | 11/2006 |
| WO | 2007080382 A1 | 7/2007 |
| WO | 2007082076 A1 | 7/2007 |
| WO | 2007082098 A2 | 7/2007 |
| WO | 2009007751 A2 | 1/2009 |
| WO | 2009023438 A1 | 2/2009 |
| WO | 2009029735 A1 | 3/2009 |
| WO | 2009081112 A2 | 7/2009 |
| WO | 2010060581 A2 | 6/2010 |
| WO | 2010092339 A1 | 8/2010 |
| WO | 2009138712 A3 | 9/2010 |
| WO | 2010125332 A1 | 11/2010 |
| WO | 2011080568 A2 | 7/2011 |
| WO | 2012080187 A1 | 6/2012 |
| WO | 2012149528 A1 | 11/2012 |
| WO | 2013003740 A1 | 1/2013 |
| WO | 2013014165 A1 | 1/2013 |

OTHER PUBLICATIONS

International Search Report and Written Opinion issued in International Application No. PCT/US2014/024749, dated Jul. 10, 2014.
International Search Report and Written Opinion issued in International Application No. PCT/US2014/024752 dated Jul. 7, 2014.
International Search Report and Written Opinion issued in related International Application No. PCY/US2015/050190 dated Dec. 29, 2015.
Abell, "Target-Site Directed Herbicide Design in, pest control with enhanced environmental safety 15-37", 1993.
Knight, et al., "Annual Review of Phytopathology", 1997.
Ruegg, et al., "Weed Research", 2006.
International Search Report and Written Opinion dated Jul. 14, 2014 in related PCT Application No. PCT/US2014/024388 (10 pages).
Extended European Search Report dated Sep. 12, 2016 in related Patent No. EP 2970186 (5 pages).
Extended European Search Report dated Oct. 14, 2016 in related Patent No. EP 2970187 (5 pages).
Extended European Search Report dated Apr. 3, 2018 in related European Application 158411143 (9 pages).
Pubchem. Substance Record for SID 172846318. Deposit Date: Mar. 7, 2013. [retrieved on Dec. 1, 2015]. Retrieved from the Internet, <URL:https://pubchem.ncbl.nlm.nih.gov/substance/172846318/version/1#section=Top>. entire document.
International Search Report and Written Opinion issued in related International Application No. PCT/US2015/050122 dated Jul. 5, 2016.

* cited by examiner

SYNERGISTIC WEED CONTROL FROM APPLICATIONS OF PYRIDINE CARBOXYLIC ACID HERBICIDES AND PHOTOSYSTEM II INHIBITORS

CROSS REFERENCE TO RELATED APPLICATIONS

This application claims benefit of U.S. Provisional Patent Application No. 62/050,712, filed Sep. 15, 2014, which is hereby incorporated herein by reference in its entirety.

FIELD OF THE DISCLOSURE

The present disclosure relates to herbicidal compositions comprising a herbicidally effective amount of (a) a pyridine carboxylic acid herbicide or an agriculturally acceptable N-oxide, salt, or ester thereof, and (b) a photosystem II inhibitor, or an agriculturally acceptable salt or ester thereof. The present disclosure also relates to methods for controlling undesirable vegetation.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

SUMMARY OF THE DISCLOSURE

Disclosed herein are herbicidal compositions. The herbicidal compositions can comprise a herbicidally effective amount of (a) a pyridine carboxylic acid herbicide or an agriculturally acceptable N-oxide, salt, or ester thereof, and (b) a photosystem II inhibitor, or an agriculturally acceptable salt or ester thereof. In some embodiments, (a) and (b) can be provided in a synergistic herbicidally effective amount. In some embodiments, the weight ratio of (a) in grams acid equivalent per hectare (g ae/ha) to (b) in grams active ingredient per hectare (g ai/ha) can be from 1:8000 to 60:1 (e.g., from 1:8000 to 5:1, from 1:1000 to 60:1, from 1:32 to 1:3.5, from 1:32 to 3.5:1, from 1:16 to 1:7, or from 1:16 to 1:1).

The pyridine carboxylic acid herbicide can comprise a compound defined by Formula (I)

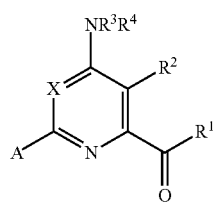

(I)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is one of groups A1 to A36

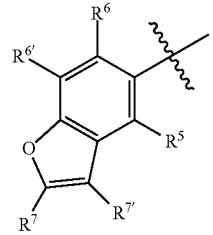

A1

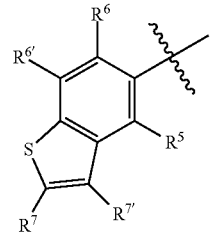

A2

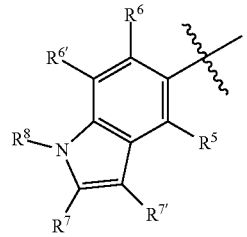

A3

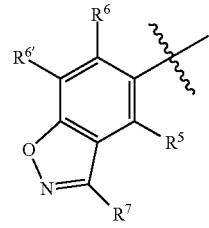

A4

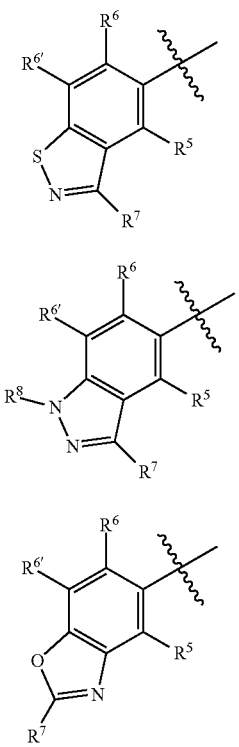
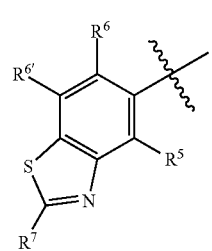
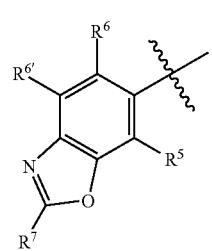
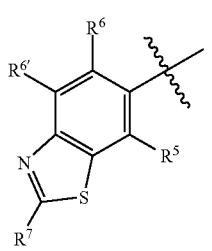
A5
A6
A7
A8
A9
A10
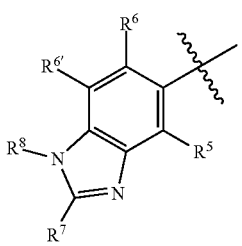
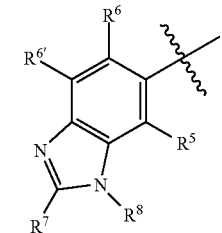
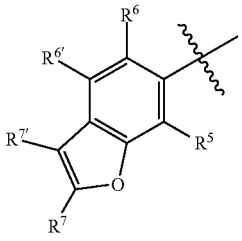
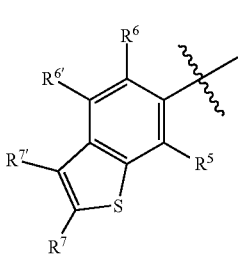
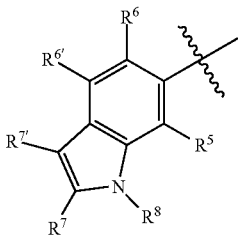
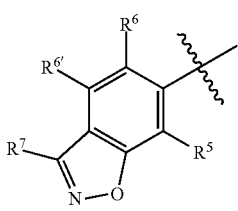
A11
A12
A13
A14
A15
A16

| | |
|---|---|
| 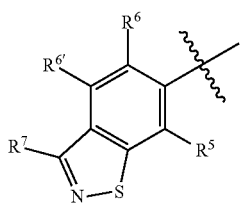 A17 | 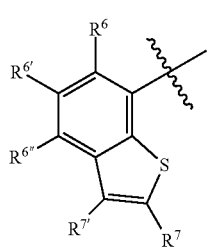 A24 |
| 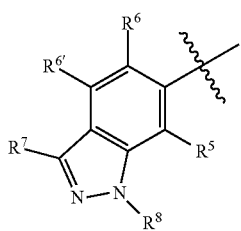 A18 | 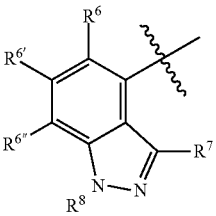 A25 |
| 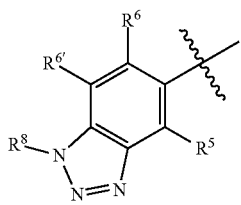 A19 | 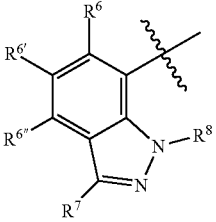 A26 |
| 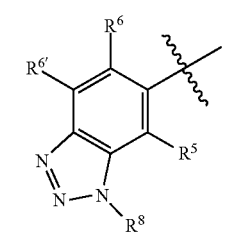 A20 | |
| 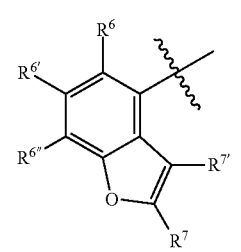 A21 | 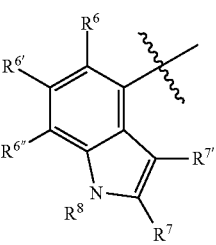 A27 |
| 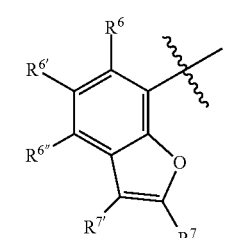 A22 | 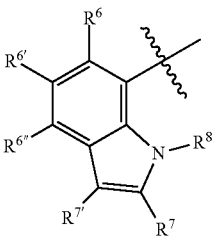 A28 |
| 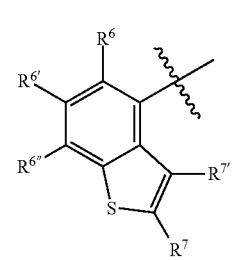 A23 | 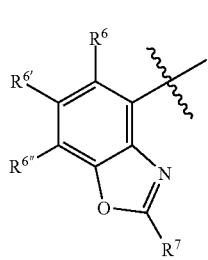 A29 |

A30 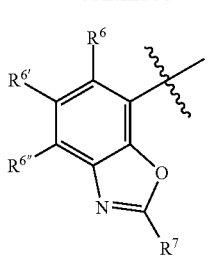

A31 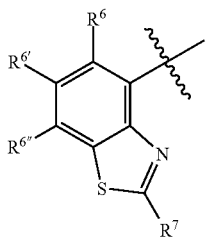

A32 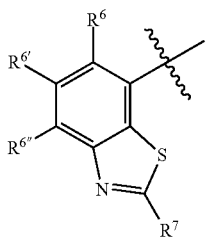

A33 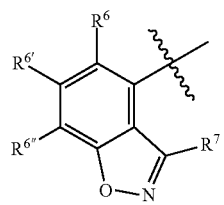

A34 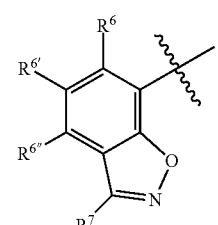

A35 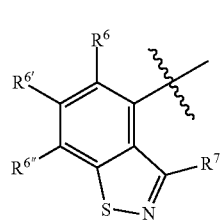

A36 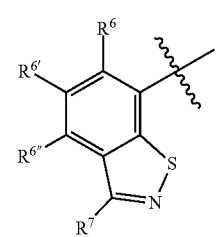

$R^5$, if applicable to the A group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In certain embodiments, the pyridine carboxylic acid herbicide can comprise a compound defined by Formula (II):

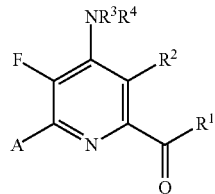
(II)

wherein $R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, $R^1$ is $OR^{1'}$, wherein $R^{1'}$ is hydrogen, $C_1$-$C_8$ alkyl, or $C_7$-$C_{10}$ arylalkyl. In certain embodiments, $R^2$ is Cl, methoxy, vinyl, or 1-propenyl; $R^3$ and $R^4$ are hydrogen; A is A15; $R^5$ is hydrogen or F; $R^6$ is hydrogen or F; and $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise a compound defined by Formula (III):

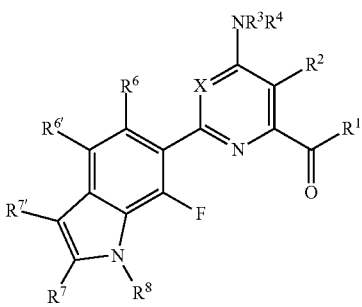

(III)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1'}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, X is N, CH or CF. In certain embodiments, X is CF, $R^1$ is $OR^{1'}$, wherein $R^{1'}$ is hydrogen, $C_1$-$C_8$ alkyl, or $C_7$-$C_{10}$ arylalkyl; $R^2$ is Cl, methoxy, vinyl, or 1-propenyl; $R^3$ and $R^4$ are hydrogen; $R^6$ is hydrogen or F; and $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can include 4-amino-3-chloro-5-fluoro-6-(7-fluoro-1H-indol-6-yl) picolinic acid, or an agriculturally acceptable N-oxide, salt, or ester thereof.

In some embodiments, (b) can comprise a nitrile herbicide. In certain embodiments, (b) can include bromoxynil or an agriculturally acceptable salt or ester thereof. In some embodiments, (b) can be a benzothiadiazinone herbicide. In certain embodiments, (b) can include bentazon or an agriculturally acceptable salt thereof. In some embodiments, (b) can be a urea herbicide. In certain embodiments, (b) can include isoproturon. In some embodiments, (b) can be a triazinone herbicide. In certain embodiments, (b) can include metribuzin or an agriculturally acceptable salt thereof. In some embodiments, (b) can be a triazine herbicide. In certain embodiments, (b) can include atrazine or an agriculturally acceptable salt thereof.

The composition can further comprise an additional pesticide, a herbicidal safener, an agriculturally acceptable adjuvant or carrier, or a combination thereof. The composition can be provided as a herbicidal concentrate.

The present disclosure also relates to methods of controlling undesirable vegetation which comprise applying to vegetation or an area adjacent the vegetation or applying to soil or water to prevent the emergence or growth of vegetation a herbicidally effective amount of (a) a pyridine carboxylic acid herbicide or an agriculturally acceptable N-oxide, salt, or ester thereof, and (b) a photosystem II inhibitor, or an agriculturally acceptable salt or ester thereof. In some embodiments, (a) and (b) are provided in a synergistically effective amount. In some embodiments, (a) and (b) are applied simultaneously. In some embodiments, (a) and (b) are applied post-emergence of the undesirable vegetation.

In some embodiments, (a) can comprise a pyridine carboxylic acid herbicide described above. In certain embodiments, (a) can comprise 4-amino-3-chloro-5-fluoro-6-(7-fluoro-1H-indol-6-yl) picolinic acid, or an agriculturally acceptable N-oxide, salt, or ester thereof. In some embodiments, (b) can comprise a nitrile herbicide. In certain embodiments, (b) can include bromoxynil or an agriculturally acceptable salt or ester thereof. In some embodiments, (b) can be a benzothiadiazinone herbicide. In certain embodiments, (b) can include bentazon or an agriculturally acceptable salt thereof. In some embodiments, (b) can be a urea herbicide. In certain embodiments, (b) can include isoproturon. In some embodiments, (b) can be a triazinone herbicide. In certain embodiments, (b) can include metribuzin or an agriculturally acceptable salt thereof. In some embodiments, (b) can comprise a triazine herbicide. In certain embodiments, (b) can include atrazine or an agriculturally acceptable salt thereof. In addition to the pyridine carboxylic acid herbicide or agriculturally acceptable N-oxide, salt or ester thereof, the compositions can include a photosystem II inhibitor.

In some cases, (a) can be applied in an amount of from 0.1 grams acid equivalent per hectare (g ae/ha) to 300 g ae/ha (e.g., from 0.5 g ae/ha to 300 g ae/ha, from 5 g ae/ha to 40 g ae/ha, from 5 g ae/ha to 15 g ae/ha) and/or (b) can be applied in an amount of from 5 grams active ingredient per hectare (g ai/ha) to 4000 g ai/ha (e.g., from 5 g ai/ha to 1000 g ai/ha, from 30 g ai/ha to 1000 g ai/ha, or from 30 g ai/ha to 300 g ai/ha). In some cases, (a) in g ae/ha and (b) in g ai/ha can be applied in a weight ratio of from 1:8000 to 60:1 (e.g., from 1:8000 to 5:1, from 1:1000 to 60:1, from 1:32 to 1:3.5, from 1:32 to 3.5:1, from 1:16 to 1:7, or from 1:16 to 1:1).

The description below sets forth details of one or more embodiments of the present disclosure. Other features, objects, and advantages will be apparent from the description and from the claims.

DETAILED DESCRIPTION

The present disclosure relates to herbicidal compositions comprising a herbicidally effective amount of (a) a pyridine carboxylic acid herbicide or an agriculturally acceptable N-oxide, salt, or ester thereof, and (b) a photosystem II inhibitor, or an agriculturally acceptable salt or ester thereof. The present disclosure also relates to methods for controlling undesirable vegetation.

I. Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix $C_n$-$C_m$ preceding a group or moiety indicates, in each case, the possible number of carbon atoms in the group or moiety that follows.

As used herein, the terms "herbicide" and "herbicidal active ingredient" refer to an active ingredient that kills, controls, or otherwise adversely modifies the growth of vegetation, particularly undesirable vegetation, such as weeds, when applied in an appropriate amount.

As used herein, a herbicidally effective amount" refers to an amount of an active ingredient that causes a "herbicidal effect," i.e., an adversely modifying effect including, for instance, a deviation from natural growth or development, killing, regulation, desiccation, growth inhibition, growth reduction, and retardation.

As used herein, applying a herbicide or herbicidal composition refers to delivering it directly to the targeted vegetation or to the locus thereof or to the area where control of undesired vegetation is desired. Methods of application include, but are not limited to pre-emergently contacting soil or water, post-emergently contacting the undesirable vegetation or area adjacent to the undesirable vegetation.

As used herein, the terms "crops" and "vegetation" can include, for instance, dormant seeds, germinant seeds, emerging seedlings, plants emerging from vegetative propagules, immature vegetation, and established vegetation.

As used herein, immature vegetation refers to small vegetative plants prior to reproductive stage, and mature vegetation refers to vegetative plants during and after the reproductive stage.

As used herein, the term "acyl" refers to a group of formula —C(O)R, where R is hydrogen, alkyl (e.g., $C_1$-$C_{10}$ alkyl), haloalkyl ($C_1$-$C_8$ haloalkyl), alkenyl ($C_2$-$C_8$ alkenyl), haloalkenyl (e.g., $C_2$-$C_8$ haloalkenyl), alkynyl (e.g., $C_2$-$C_8$ alkynyl), alkoxy ($C_1$-$C_8$ alkoxy), haloalkoxy ($C_1$-$C_8$ alkoxy), aryl, or heteroaryl, arylalkyl ($C_7$-$C_{10}$ arylalkyl), as defined below, where "C(O)" or "CO" is short-hand notation for C=O. In some embodiments, the acyl group can be a $C_1$-$C_6$ acyl group (e.g., a formyl group, a $C_1$-$C_5$ alkylcarbonyl group, or a $C_1$-$C_5$ haloalkylcarbonyl group). In some embodiments, the acyl group can be a $C_1$-$C_3$ acyl group (e.g., a formyl group, a $C_1$-$C_3$ alkylcarbonyl group, or a $C_1$-$C_3$ haloalkylcarbonyl group).

As used herein, the term "alkyl" refers to saturated, straight-chained or branched saturated hydrocarbon moieties. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples of alkyl groups include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl. Alkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "haloalkyl" refers to straight-chained or branched alkyl groups, wherein these groups the hydrogen atoms may partially or entirely be substituted with halogen atoms. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl, and 1,1,1-trifluoroprop-2-yl. Haloalkyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "alkenyl" refers to unsaturated, straight-chained, or branched hydrocarbon moieties containing a double bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=CH$_2$; 1-propenyl refers to a group with the structure —CH=CH—CH$_3$; and 2-propenyl refers to a group with the structure —CH$_2$—CH=CH$_2$. Alkenyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

The term "haloalkenyl," as used herein, refers to an alkenyl group, as defined above, which is substituted by one or more halogen atoms.

As used herein, the term "alkynyl" represents straight-chained or branched hydrocarbon moieties containing a triple bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, hydroxy, nitro, cyano, formyl, $C_1$-$C_6$ alkoxy, $C_1$-$C_6$ haloalkoxy, $C_1$-$C_6$ acyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkoxycarbonyl, $C_1$-$C_6$ haloalkoxycarbonyl, $C_1$-$C_6$ carbamoyl, $C_1$-$C_6$ halocarbamoyl, hydroxycarbonyl, $C_1$-$C_6$ alkylcarbonyl, $C_1$-$C_6$ haloalkylcarbonyl, aminocarbonyl, $C_1$-$C_6$ alkylaminocarbonyl, haloalkylaminocarbonyl, $C_1$-$C_6$ dialkylaminocarbonyl, and $C_1$-$C_6$ dihaloalkylaminocarbonyl, provided that the substituents are sterically compatible and the rules of chemical bonding and strain energy are satisfied. Preferred substituents include cyano and $C_1$-$C_6$ alkoxy.

As used herein, the term "alkoxy" refers to a group of the formula R—O—, where R is unsubstituted or substituted alkyl as defined above. Unless otherwise specified, alkoxy groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, the term "haloalkoxy" refers to a group of the formula R—O—, where R is unsubstituted or substituted haloalkyl as defined above. Unless otherwise specified, haloalkoxy groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) haloalkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, and 1,1,1-trifluoroprop-2-oxy.

As used herein, the term "alkylthio" refers to a group of the formula R—S—, where R is unsubstituted or substituted alkyl as defined above. Unless otherwise specified, alkylthio groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-di-methylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methyl-pentylthio, 1,1-dimethylbutylthio, 1,2-dimethyl-butylthio, 1,3-dimethyl-butylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methyl propylthio, and 1-ethyl-2-methylpropylthio.

As used herein, the term "haloalkylthio" refers to an alkylthio group as defined above wherein the carbon atoms are partially or entirely substituted with halogen atoms. Unless otherwise specified, haloalkylthio groups wherein R is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include chloromethylthio, bromomethylthio, dichloromethylthio, trichloromethylthio, fluoromethylthio, difluoromethylthio, trifluoromethylthio, chlorofluoromethylthio, dichlorofluoro-methylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

As used herein, the term "aryl," as well as derivative terms such as aryloxy, refers to groups that include a monovalent aromatic carbocyclic group of from 6 to 14 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more chemical moieties. Examples of suitable substituents include, for example, hydroxy, halogen, nitro, cyano, formyl, $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, $C_1$-$C_6$ acyl, $C_1$-$C_6$ alkylthio, $C_1$-$C_6$ alkylsulfinyl, $C_1$-$C_6$ alkylsulfonyl, $C_1$-$C_6$ alkoxycarbonyl, $C_1$-$C_6$ carbamoyl, hydroxycarbonyl, $C_1$-$C_6$ alkylcarbonyl, aminocarbonyl, $C_1$-$C_6$ alkylaminocarbonyl, $C_1$-$C_6$ dialkylaminocarbonyl, provided that the substituents are sterically compatible and the rules of chemical bonding and strain energy are satisfied. Preferred substituents include halogen, $C_1$-$C_2$ alkyl and $C_1$-$C_2$ haloalkyl.

As used herein, the term "alkylcarbonyl" refers to an unsubstituted or substituted alkyl group bonded to a carbonyl group. $C_1$-$C_3$ alkylcarbonyl and $C_1$-$C_3$ haloalkylcarbonyl refer to groups wherein a $C_1$-$C_3$ unsubstituted or substituted alkyl or haloalkyl group is bonded to a carbonyl group (the group contains a total of 2 to 4 carbon atoms).

As used herein, the term "alkoxycarbonyl" refers to a group of the formula

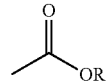

wherein R is unsubstituted or substituted alkyl.

As used herein, the term "arylalkyl" refers to an alkyl group substituted with an unsubstituted or substituted aryl group. $C_7$-$C_{10}$ arylalkyl refers to a group wherein the total number of carbon atoms in the group is 7 to 10, not including the carbon atoms present in any substituents of the aryl group.

As used herein, the term "alkylamino" refers to an amino group substituted with one or two unsubstituted or substituted alkyl groups, which may be the same or different.

As used herein, the term "haloalkylamino" refers to an alkylamino group wherein the alkyl carbon atoms are partially or entirely substituted with halogen atoms.

As used herein, $C_1$-$C_6$ alkylaminocarbonyl refers to a group of the formula RNHC(O)— wherein R is $C_1$-$C_6$ unsubstituted or substituted alkyl, and $C_1$-$C_6$ dialkylaminocarbonyl refers to a group of the formula $R_2NC(O)$— wherein each R is independently $C_1$-$C_6$ unsubstituted or substituted alkyl.

As used herein, the term "alkylcarbamyl" refers to a carbamyl group substituted on the nitrogen with an unsubstituted or substituted alkyl group.

As used herein, the term "alkylsulfonyl" refers to a group of the formula

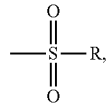

where R is unsubstituted or substituted alkyl.

As used herein, the term "carbamyl" (also referred to as carbamoyl and aminocarbonyl) refers to a group of the formula $H_2N$

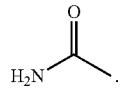

As used herein, the term "dialkylphosphonyl" refers to a group of the formula

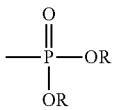

where R is independently unsubstituted or substituted alkyl in each occurrence.

As used herein, $C_1$-$C_6$ trialkylsilyl refers to a group of the formula —$SiR_3$ wherein each R is independently a $C_1$-$C_6$ unsubstituted or substituted alkyl group (the group contains a total of 3 to 18 carbon atoms).

As used herein, Me refers to a methyl group; OMe refers to a methoxy group; and i-Pr refers to an isopropyl group.

As used herein, the term "halogen" including derivative terms such as "halo" refers to fluorine, chlorine, bromine and iodine.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can be hydrolyzed, oxidized, metabolized, or otherwise converted, e.g., in plants, water, or soil, to the corresponding carboxylic acid which, depending on the pH, may be in the dissociated or undissociated form.

Compounds described herein can include N-oxides. Pyridine N-oxides can be obtained by oxidation of the corresponding pyridines. Suitable oxidation methods are described, for example, in Houben-Weyl, *Methoden der organischen Chemie*[*Methods in organic chemistry*], expanded and subsequent volumes to the 4th edition, volume E 7b, p. 565 f.

Pyridine Carboxylic Acid Herbicides

Compositions and methods of the present disclosure can include a pyridine carboxylic acid herbicide defined by Formula (I)

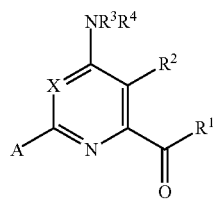

(I)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $-CR^{17}=CR^{18}-SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with $=C$ represent a 5- or 6-membered saturated ring;

A is one of groups A1 to A36

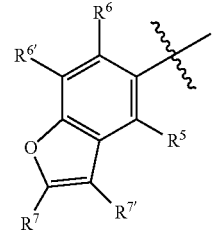
A1

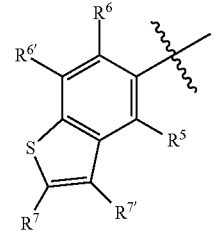
A2

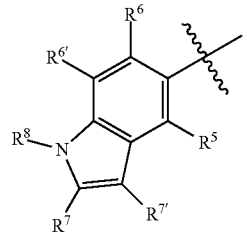
A3

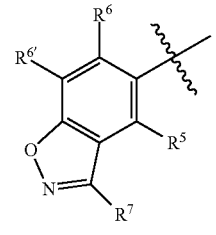
A4

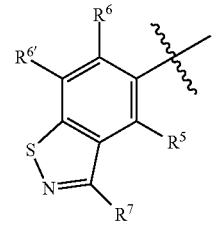
A5

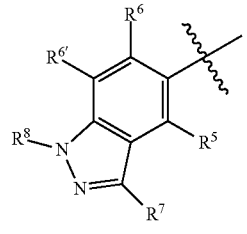
A6

-continued
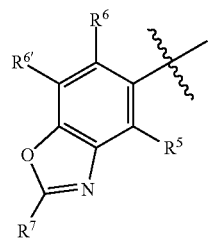 A7
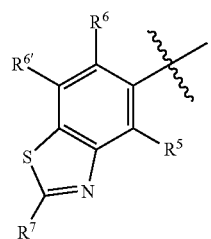 A8
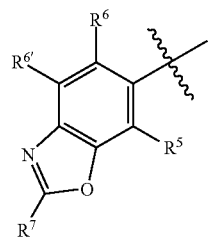 A9
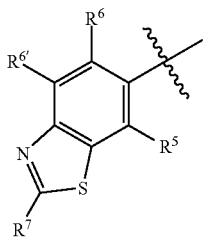 A10
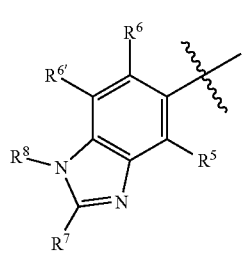 A11
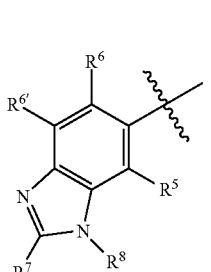 A12
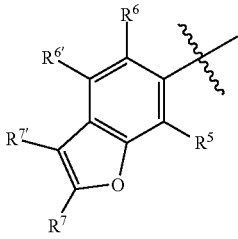 A13
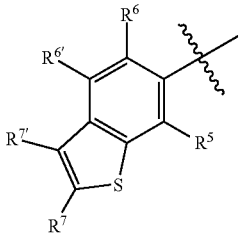 A14
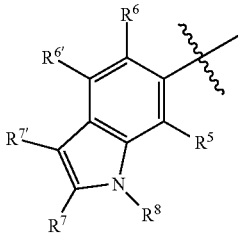 A15
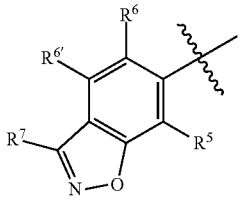 A16
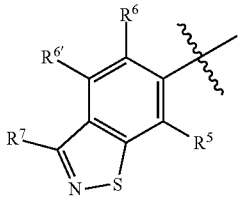 A17
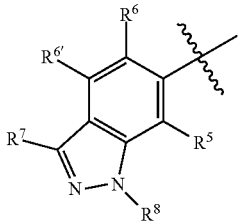 A18
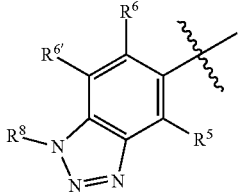 A19

-continued
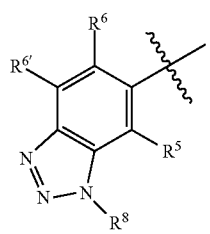
A20
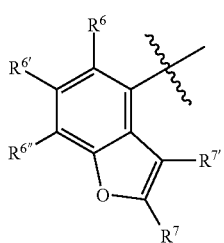
A21
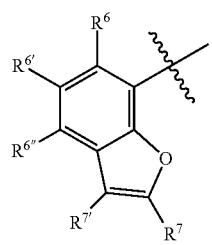
A22
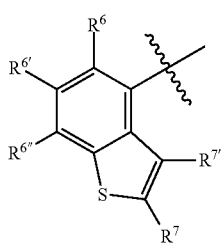
A23
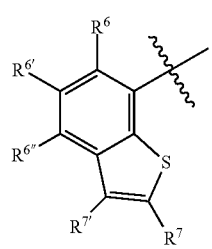
A24
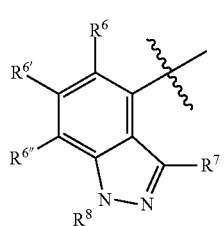
A25
-continued
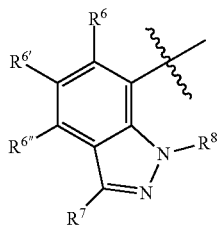
A26
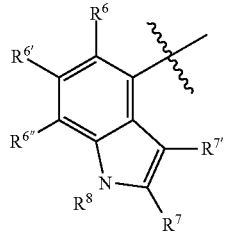
A27
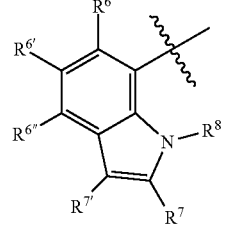
A28
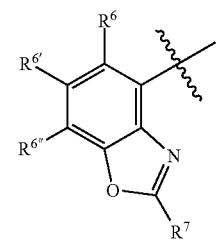
A29
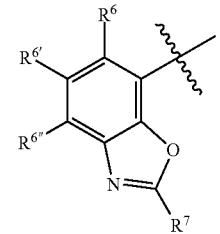
A30
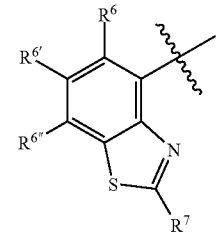
A31

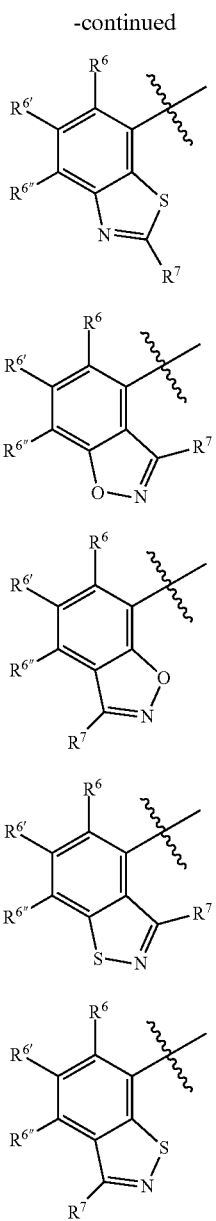

A32

A33

A34

A35

A36

$R^5$, if applicable to the A group, is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$, if applicable to the A group, are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_1$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments, $R^1$ is $OR^{1'}$, wherein $R^{1'}$ is hydrogen, $C_1$-$C_8$ alkyl, or $C_7$-$C_{10}$ arylalkyl. In some embodiments, $R^{1'}$ is hydrogen or $C_1$-$C_8$ alkyl. In some embodiments, $R^{1'}$ is hydrogen.

In some embodiments, $R^2$ is halogen, $C_1$-$C_4$ alkyl, $C_1$-$C_4$ haloalkyl, $C_2$-$C_4$ alkynyl, $C_2$-$C_4$-alkenyl, $C_2$-$C_4$ haloalkenyl, $C_1$-$C_4$-alkoxy, or $C_1$-$C_4$ haloalkoxy. In some embodiments, $R^2$ is halogen, $C_2$-$C_4$-alkenyl, $C_2$-$C_4$ haloalkenyl, or $C_1$-$C_4$-alkoxy. In some embodiments, $R^2$ is halogen. In some embodiments, $R^2$ is $C_2$-$C_4$-alkenyl or $C_2$-$C_4$ haloalkenyl. In some embodiments, $R^2$ is $C_1$-$C_4$ alkoxy. In some embodiments, $R^2$ is Cl, OMe, vinyl, or 1-propenyl. In some embodiments, $R^2$ is Cl. In some embodiments, $R^2$ is OMe. In some embodiments, $R^2$ is vinyl or 1-propenyl.

In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy, or $C_1$-$C_6$ alkylamino. In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, or $R^3$ and $R^4$ taken together represent $=CR^{3'}(R^{4'})$, wherein $R^{3'}$ and $R^{4'}$ are independently hydrogen, $C_1$-$C_6$ alkyl, $C_1$-$C_6$ alkoxy or $C_1$-$C_6$ alkylamino.

In some embodiments, $R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, formyl, $C_1$-$C_3$ alkylcarbonyl, or $C_1$-$C_3$ haloalkylcarbonyl. In some embodiments, at least one of $R^3$ and $R^4$ are hydrogen. In some embodiments, $R^3$ and $R^4$ are both hydrogen.

In some embodiments, X is N, CH or CF. In some embodiments, X is N. In some embodiments, X is CH. In some embodiments, X is CF. In other embodiments, X is C—$CH_3$.

In some embodiments, A is A1, A2, A3, A4, A5, A6, A7, A8, A9, A10, A11, A12, A13, A14, A15, A16, A17, A18, A19, or A20. In other embodiments, A is one of A21, A22, A23, A24, A25, A26, A27, A28, A29, A30, A31, A32, A33, A34, A35, and A36.

In some embodiments, A is one of groups A1, A2, A3, A7, A8, A9, A10, A13, A14, and A15. In some embodiments, A is one of groups A1, A2, A3, A13, A14, and A15. In some embodiments, A is one of groups A13, A14, and A15. In some embodiments, A is A15.

In some embodiments, $R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, $C_1$-$C_3$ haloalkylthio, or amino. In some embodiments, $R^5$ is hydrogen, halogen, $C_1$-$C_4$ alkyl, $C_1$-$C_4$ haloalkyl, $C_1$-$C_3$ alkoxy, $C_1$-$C_3$ haloalkoxy, or amino. In some embodiments, $R^5$ is hydrogen, halogen, $C_1$-$C_4$ alkyl or $C_1$-$C_4$ alkoxy. In some embodiments, $R^5$ is hydrogen or F. In some embodiments, $R^5$ is hydrogen.

In other embodiments, $R^5$ is F.

In some embodiments, $R^6$ is hydrogen, halogen, $C_1$-$C_4$ alkyl, $C_1$-$C_4$ haloalkyl, $C_1$-$C_3$ alkoxy, or $C_1$-$C_3$ haloalkoxy. In some embodiments, $R^6$ is hydrogen or fluorine. In some embodiments, $R^6$ is hydrogen. In some embodiments, $R^6$ is fluorine.

In some embodiments, $R^{6'}$ is hydrogen or halogen. In some embodiments, $R^{6'}$ is hydrogen, F, or Cl. In some embodiments, $R^{6'}$ is hydrogen or F. In some embodiments, $R^{6'}$ is hydrogen.

In some embodiments, $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$. In some embodiments, $R^{6''}$ is hydrogen. In some embodiments, $R^{6''}$ is halogen. In some embodiments, $R^{6''}$ is $C_1$-$C_4$ alkyl. In some embodiments, $R^{6''}$ is $C_1$-$C_4$ haloalkyl. In some embodiments, $R^{6''}$ is cyclopropyl. In some embodiments, $R^{6''}$ is $C_2$-$C_4$ alkynyl. In some embodiments, $R^{6''}$ is CN. In some embodiments, $R^{6''}$ is $NO_2$.

In some embodiments:
X is N, CH, CF, CCl, or CBr;
$R^1$ is $OR^{1'}$, wherein $R^{1'}$ is hydrogen or $C_1$-$C_4$ alkyl;
$R^2$ is chlorine;
$R^3$ and $R^4$ are hydrogen;
A is A1, A2, A3, A4, A5, A6, A7, A8, A9, A10, A11, A12, A13, A14, A15, A16, A17, A18, A19, or A20;
$R^5$ is hydrogen, halogen, OH, amino, CN, $C_1$-$C_3$ alkyl, $C_1$-$C_3$ alkoxy, $C_1$-$C_3$ alkylamino, or cyclopropyl;
$R^6$, $R^{6'}$, and $R^{6''}$ are independently hydrogen, halogen, OH, $NH_2$, CN, $C_1$-$C_3$ alkyl, $C_1$-$C_3$ alkoxy, cyclopropyl, or vinyl;
$R^7$ and $R^{7'}$ are independently hydrogen, halogen, $C_1$-$C_3$ alkyl, $C_1$-$C_3$ alkoxy, $C_1$-$C_3$ alkylthio, cyclopropyl, $C_1$-$C_3$ alkylamino, or phenyl; and
$R^8$ is hydrogen, $C_1$-$C_3$ alkyl, phenyl, or $C_1$-$C_3$ alkylcarbonyl.

In some embodiments, $R^2$ is halogen, $C_2$-$C_4$-alkenyl, $C_2$-$C_4$ haloalkenyl, or $C_1$-$C_4$-alkoxy; $R^3$ and $R^4$ are both hydrogen; and X is N, CH, or CF.

In some embodiments, $R^2$ is halogen; $R^3$ and $R^4$ are both hydrogen; and X is N, CH, or CF.

In some embodiments, $R^2$ is $C_2$-$C_4$-alkenyl or $C_2$-$C_4$ haloalkenyl; $R^3$ and $R^4$ are both hydrogen; and X is N, CH, or CF.

In some embodiments, $R^2$ is $C_1$-$C_4$-alkoxy; $R^3$ and $R^4$ are both hydrogen; and X is N, CH, or CF.

In some embodiments, $R^2$ is halogen, $C_2$-$C_4$-alkenyl, $C_2$-$C_4$ haloalkenyl, or $C_1$-$C_4$-alkoxy; $R^3$ and $R^4$ are both hydrogen; X is N, CH, or CF; $R^5$ is hydrogen or F; $R^6$ is hydrogen or F; $R^{6'}$ is hydrogen; $R^{6''}$, if applicable to the relevant A group, is hydrogen or halogen; and $R^7$ and $R^{7'}$, if applicable to the relevant A group, are independently hydrogen or halogen.

In some embodiments, $R^2$ is halogen, $C_1$-$C_4$-alkoxy, or $C_2$-$C_4$-alkenyl; $R^3$ and $R^4$ are hydrogen; X is N, CH, or CF; and A is one of groups A1 to A20.

In some embodiments, $R^2$ is chlorine; $R^3$ and $R^4$ are hydrogen; X is N, CH, or CF; A is one of groups A1 to A20; $R^5$ is hydrogen or F; $R^6$ and $R^{6'}$ are independently hydrogen or F; and $R^7$ and $R^{7'}$, if applicable to the relevant A group, are independently hydrogen, halogen, $C_1$-$C_4$ alkyl, or $C_1$-$C_4$ haloalkyl.

In some embodiments, $R^2$ is chlorine, methoxy, vinyl, or 1-propenyl; $R^3$ and $R^4$ are hydrogen; and X is N, CH, or CF.

In some embodiments, $R^2$ is chlorine; $R^3$ and $R^4$ are hydrogen; and X is N, CH, or CF.

In some embodiments, $R^2$ is vinyl or 1-propenyl; $R^3$ and $R^4$ are hydrogen; and X is N, CH, or CF.

In some embodiments, $R^2$ is methoxy; $R^3$ and $R^4$ are hydrogen; and X is N, CH, or CF.

In some embodiments, $R^2$ is chlorine; $R^3$ and $R^4$ are hydrogen; and X is N.

In some embodiments, $R^2$ is chlorine; $R^3$ and $R^4$ are hydrogen; and X is CH.

In some embodiments, $R^2$ is chlorine; $R^3$ and $R^4$ are hydrogen; and X is CF.

In some embodiments, $R^2$ is chlorine; $R^3$ and $R^4$ are hydrogen; X is CF; A is one of A1, A2, A3, A7, A8, A9, A10, A13, A14, or A15; $R^5$ is F; and $R^6$ is H.

In some embodiments, $R^2$ is chlorine, methoxy, vinyl, or 1-propenyl; $R^3$ and $R^4$ are hydrogen; X is N, CH, or CF; and A is one of A21 to A36.

In some embodiments, $R^2$ is chlorine, methoxy, vinyl, or 1-propenyl; $R^3$ and $R^4$ are hydrogen; X is CF; and A is one of

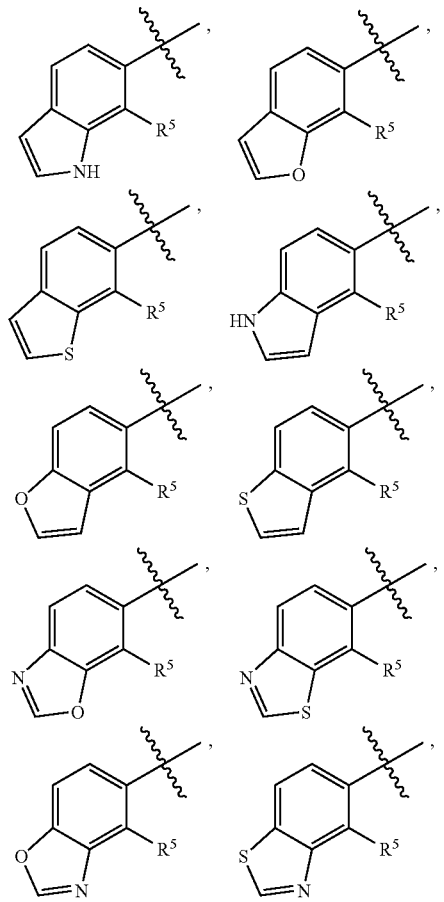

wherein $R^5$ is hydrogen or F.

In some embodiments, $R^2$ is chlorine, methoxy, vinyl, or 1-propenyl; $R^3$ and $R^4$ are hydrogen; X is N, CH, or CF; and A is

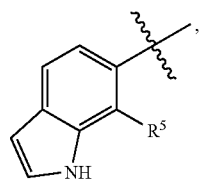

where $R^5$ is hydrogen or F.

In some embodiments, $R^2$ is chlorine, methoxy, vinyl, or 1-propenyl; $R^3$ and $R^4$ are hydrogen; X is N, CH, or CF; and A is

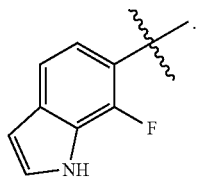 [SMILES: *c1ccc2cc[nH]c2c1F]

In some embodiments, $R^2$ is chlorine, methoxy, vinyl, or 1-propenyl; $R^3$ and $R^4$ are hydrogen; X is CF; and A is

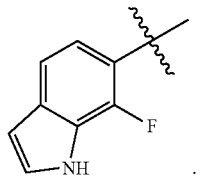

In some embodiments, the pyridine carboxylic acid herbicide can comprise a compound defined by Formula (I)

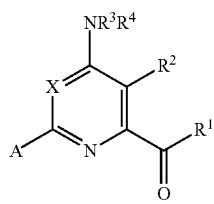

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula $—CR^{17}=CR^{18}—SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof, with the proviso that the pyridine carboxylic acid herbicide is not a compound defined by Formula (I)

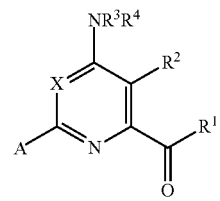

wherein

X is N, CH, CF, CCl, or CBr;

$R^1$ is $OR^{1'}$, wherein $R^{1'}$ is hydrogen or $C_1$-$C_4$ alkyl;

$R^2$ is chlorine;

$R^3$ and $R^4$ are hydrogen;

A is A1, A2, A3, A4, A5, A6, A7, A8, A9, A10, A11, A12, A13, A14, A15, A16, A17, A18, A19, or A20;

$R^5$ is hydrogen, halogen, OH, amino, CN, $C_1$-$C_3$ alkyl, $C_1$-$C_3$ alkoxy, $C_1$-$C_3$ alkylamino, or cyclopropyl;

$R^6$, $R^{6'}$, and $R^{6''}$ are independently hydrogen, halogen, OH, $NH_2$, CN, $C_1$-$C_3$ alkyl, $C_1$-$C_3$ alkoxy, cyclopropyl, or vinyl;

$R^7$ and $R^{7'}$ are independently hydrogen, halogen, $C_1$-$C_3$ alkyl, $C_1$-$C_3$ alkoxy, $C_1$-$C_3$ alkylthio, cyclopropyl, $C_1$-$C_3$ alkylamino, or phenyl; and $R^8$ is hydrogen, $C_1$-$C_3$ alkyl, phenyl, or $C_1$-$C_3$ alkylcarbonyl;

or an agriculturally acceptable N-oxide or salt thereof.

In some of these embodiments, $R^1$ is $OR^1$. In some of these embodiments, X is CF. In some of these embodiments, A is A15. In some of these embodiments, $R^5$ is F.

In some embodiments:

X is CY, wherein Y is $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is $C_5$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl;

$R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is F, Br, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}$($R^{4'}$), wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, or A20;

$R^5$ is $C_1$-$C_4$ alkyl, $C_1$-$C_4$ haloalkyl, halocyclopropyl, $C_2$-$C_4$ alkenyl, $C_2$-$C_4$ haloalkenyl, $C_2$-$C_4$ alkynyl, $C_1$-$C_3$ haloalkoxy, $C_1$-$C_3$ alkylthio, $C_1$-$C_3$ haloalkylthio, $C_1$-$C_4$ alkylamino, or $C_2$-$C_4$ haloalkylamino;

$R^6$, $R^{6'}$, and $R^{6''}$ are independently hydrogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl.

In some of these embodiments, $R^1$ is $OR^1$. In some of these embodiments, X is CF. In some of these embodiments, A is A15. In some of these embodiments, $R^5$ is F.

In some embodiments:

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio, or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —CR$^{17}$=CR$^{18}$—SiR$^{19}$R$^{20}$R$^{21}$, wherein R$^{17}$ is hydrogen, F, or Cl; R$^{18}$ is hydrogen, F, Cl, C$_1$-C$_4$ alkyl, or C$_1$-C$_4$ haloalkyl; and R$^{19}$, R$^{20}$, and R$^{21}$ are independently C$_1$-C$_{10}$ alkyl, C$_3$-C$_6$ cycloalkyl, phenyl, substituted phenyl, C$_1$-C$_{10}$ alkoxy, or OH;

R$^3$ and R$^4$ are independently hydrogen, C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, formyl, C$_1$-C$_3$ alkylcarbonyl, C$_1$-C$_3$ haloalkylcarbonyl, C$_1$-C$_6$ alkoxycarbonyl, C$_1$-C$_6$ alkylcarbamyl, C$_1$-C$_6$ alkylsulfonyl, C$_1$-C$_6$ trialkylsilyl, C$_1$-C$_6$ dialkylphosphonyl, or R$^3$ and R$^4$ taken together with N is a 5- or 6-membered saturated ring, or R$^3$ and R$^4$ taken together represent =CR$^{3'}$(R$^{4'}$), wherein R$^{3'}$ and R$^{4'}$ are independently hydrogen, C$_1$-C$_6$ alkyl, C$_3$-C$_6$ alkenyl, C$_3$-C$_6$ alkynyl, C$_1$-C$_6$ alkoxy or C$_1$-C$_6$ alkylamino, or, R$^{3'}$ and R$^{4'}$ taken together with =C represent a 5- or 6-membered saturated ring;

A is A1, A2, A3, A4, A5, A6, A7, A8, A9, A10, A11, A12, A13, A14, A15, A16, A17, or A18;

R$^5$ is hydrogen, halogen, C$_1$-C$_4$ alkyl, C$_1$-C$_4$ haloalkyl, cyclopropyl, halocyclopropyl, C$_2$-C$_4$ alkenyl, C$_2$-C$_4$ haloalkenyl, C$_2$-C$_4$ alkynyl, C$_1$-C$_3$ alkoxy, C$_1$-C$_3$ haloalkoxy, C$_1$-C$_3$ alkylthio, C$_1$-C$_3$ haloalkylthio, amino, C$_1$-C$_4$ alkylamino, C$_2$-C$_4$ haloalkylamino, OH, or CN;

R$^6$, R$^{6'}$, and R$^{6''}$ are independently hydrogen, halogen, C$_1$-C$_4$ alkyl, C$_1$-C$_4$ haloalkyl, cyclopropyl, halocyclopropyl, C$_2$-C$_4$ alkenyl, C$_2$-C$_4$ haloalkenyl, C$_2$-C$_4$ alkynyl, C$_1$-C$_3$ alkoxy, C$_1$-C$_3$ haloalkoxy, C$_1$-C$_3$ alkylthio, C$_1$-C$_3$ haloalkylthio, amino, C$_1$-C$_4$ alkylamino or C$_2$-C$_4$ haloalkylamino, OH, CN, or NO$_2$;

R$^7$ and R$^{7'}$ are independently C$_1$-C$_4$ alkyl, C$_1$-C$_4$ haloalkyl, halocyclopropyl, C$_2$-C$_4$ alkenyl, C$_2$-C$_4$ haloalkenyl, C$_2$-C$_4$ alkynyl, C$_1$-C$_3$ haloalkoxy, C$_1$-C$_3$ haloalkylthio, amino, C$_1$-C$_4$ alkylamino, or C$_2$-C$_4$ haloalkylamino; and R$^8$ is hydrogen, C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, formyl, C$_1$-C$_3$ alkylcarbonyl, C$_1$-C$_3$ haloalkylcarbonyl, C$_1$-C$_6$ alkoxycarbonyl, C$_1$-C$_6$ alkylcarbamyl, C$_1$-C$_6$ alkylsulfonyl, C$_1$-C$_6$ trialkylsilyl, or phenyl.

In some of these embodiments, R$^1$ is OR$^1$. In some of these embodiments, X is CF. In some of these embodiments, A is A15. In some of these embodiments, R$^5$ is F.

In some embodiments:

X is N or CY, wherein Y is hydrogen, halogen, C$_1$-C$_3$ alkyl, C$_1$-C$_3$ haloalkyl, C$_1$-C$_3$ alkoxy, C$_1$-C$_3$ haloalkoxy, C$_1$-C$_3$ alkylthio, or C$_1$-C$_3$ haloalkylthio;

R$^1$ is OR$^{1'}$ or NR$^{1''}$R$^{1'''}$, wherein R$^{1'}$ is hydrogen, C$_1$-C$_8$ alkyl, or C$_7$-C$_{10}$ arylalkyl, and R$^{1''}$ and R$^{1'''}$ are independently hydrogen, C$_1$-C$_{12}$ alkyl, C$_3$-C$_{12}$ alkenyl, or C$_3$-C$_{12}$ alkynyl;

R$^2$ is halogen, C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_1$-C$_4$ alkoxy, C$_1$-C$_4$ haloalkoxy, C$_1$-C$_4$ alkylthio, C$_1$-C$_4$ haloalkylthio, amino, C$_1$-C$_4$ alkylamino, C$_2$-C$_4$ haloalkylamino, formyl, C$_1$-C$_3$ alkylcarbonyl, C$_1$-C$_3$ haloalkylcarbonyl, cyano, or a group of the formula —CR$^{17}$=CR$^{18}$—SiR$^{19}$R$^{20}$R$^{21}$, wherein R$^{17}$ is hydrogen, F, or Cl; R$^{18}$ is hydrogen, F, Cl, C$_1$-C$_4$ alkyl, or C$_1$-C$_4$ haloalkyl; and R$^{19}$, R$^{20}$, and R$^{21}$ are independently C$_1$-C$_{10}$ alkyl, C$_3$-C$_6$ cycloalkyl, phenyl, substituted phenyl, C$_1$-C$_{10}$ alkoxy, or OH;

R$^3$ and R$^4$ are independently hydrogen, C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, formyl, C$_1$-C$_3$ alkylcarbonyl, C$_1$-C$_3$ haloalkylcarbonyl, C$_1$-C$_6$ alkoxycarbonyl, C$_1$-C$_6$ alkylcarbamyl, C$_1$-C$_6$ alkylsulfonyl, C$_1$-C$_6$ trialkylsilyl, C$_1$-C$_6$ dialkylphosphonyl, or R$^3$ and R$^4$ taken together with N is a 5- or 6-membered saturated ring, or R$^3$ and R$^4$ taken together represent =CR$^{3'}$(R$^{4'}$), wherein R$^{3'}$ and R$^{4'}$ are independently hydrogen, C$_1$-C$_6$ alkyl, C$_3$-C$_6$ alkenyl, C$_3$-C$_6$ alkynyl, C$_1$-C$_6$ alkoxy or C$_1$-C$_6$ alkylamino, or, R$^{3'}$ and R$^{4'}$ taken together with =C represent a 5- or 6-membered saturated ring;

A is A3, A6, A11, A12, A15, A18, A19, or A20;

R$^5$ is hydrogen, halogen, C$_1$-C$_4$ alkyl, C$_1$-C$_4$ haloalkyl, cyclopropyl, halocyclopropyl, C$_2$-C$_4$ alkenyl, C$_2$-C$_4$ haloalkenyl, C$_2$-C$_4$ alkynyl, C$_1$-C$_3$ alkoxy, C$_1$-C$_3$ haloalkoxy, C$_1$-C$_3$ alkylthio, C$_1$-C$_3$ haloalkylthio, amino, C$_1$-C$_4$ alkylamino, C$_2$-C$_4$ haloalkylamino, OH, or CN;

R$^6$, R$^{6'}$, and R$^{6''}$ are independently hydrogen, halogen, C$_1$-C$_4$ alkyl, C$_1$-C$_4$ haloalkyl, cyclopropyl, halocyclopropyl, C$_2$-C$_4$ alkenyl, C$_2$-C$_4$ haloalkenyl, C$_2$-C$_4$ alkynyl, C$_1$-C$_3$ alkoxy, C$_1$-C$_3$ haloalkoxy, C$_1$-C$_3$ alkylthio, C$_1$-C$_3$ haloalkylthio, amino, C$_1$-C$_4$ alkylamino or C$_2$-C$_4$ haloalkylamino, OH, CN, or NO$_2$;

R$^7$ and R$^{7'}$ are independently hydrogen, halogen, C$_1$-C$_4$ alkyl, C$_1$-C$_4$ haloalkyl, cyclopropyl, halocyclopropyl, C$_2$-C$_4$ alkenyl, C$_2$-C$_4$ haloalkenyl, C$_2$-C$_4$ alkynyl, C$_1$-C$_3$ alkoxy, C$_1$-C$_3$ haloalkoxy, C$_1$-C$_3$ alkylthio, C$_1$-C$_3$ haloalkylthio, amino, C$_1$-C$_4$ alkylamino, C$_2$-C$_4$ haloalkylamino, or phenyl; and R$^8$ is C$_3$-C$_6$ alkyl, C$_1$-C$_6$ haloalkyl, C$_3$-C$_6$ alkenyl, C$_3$-C$_6$ haloalkenyl, C$_3$-C$_6$ alkynyl, formyl, C$_1$-C$_3$ haloalkylcarbonyl, C$_1$-C$_6$ alkoxycarbonyl, C$_1$-C$_6$ alkylcarbamyl, C$_1$-C$_6$ alkylsulfonyl, or C$_1$-C$_6$ trialkylsilyl.

In some of these embodiments, R$^1$ is OR$^1$. In some of these embodiments, X is CF. In some of these embodiments, A is A15. In some of these embodiments, R$^5$ is F.

In certain embodiments, the pyridine carboxylic acid herbicide can comprise a compound defined by Formula (II):

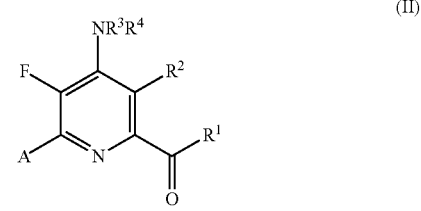

(II)

wherein

R$^1$ is OR$^{1'}$ or NR$^{1''}$R$^{1'''}$, wherein R$^{1'}$ is hydrogen, C$_1$-C$_8$ alkyl, or C$_7$-C$_{10}$ arylalkyl, and R$^{1''}$ and R$^{1'''}$ are independently hydrogen, C$_1$-C$_{12}$ alkyl, C$_3$-C$_{12}$ alkenyl, or C$_3$-C$_{12}$ alkynyl;

R$^2$ is halogen, C$_1$-C$_4$ alkyl, C$_1$-C$_4$ haloalkyl, C$_2$-C$_4$ alkenyl, C$_2$-C$_4$ haloalkenyl, C$_2$-C$_4$ alkynyl, C$_1$-C$_4$ alkoxy, C$_1$-C$_4$ haloalkoxy, C$_1$-C$_4$ alkylthio, C$_1$-C$_4$ haloalkylthio, amino, C$_1$-C$_4$ alkylamino, C$_2$-C$_4$ haloalkylamino, formyl, C$_1$-C$_3$ alkylcarbonyl, C$_1$-C$_3$ haloalkylcarbonyl, cyano, or a group of the formula —CR$^{17}$=CR$^{18}$—SiR$^{19}$R$^{20}$R$^{21}$, wherein R$^{17}$ is hydrogen, F, or Cl; R$^{18}$ is hydrogen, F, Cl, C$_1$-C$_4$ alkyl, or C$_1$-C$_4$ haloalkyl; and R$^{19}$, R$^{20}$, and R$^{21}$ are independently C$_1$-C$_{10}$ alkyl, C$_3$-C$_6$ cycloalkyl, phenyl, substituted phenyl, C$_1$-C$_{10}$ alkoxy, or OH;

R$^3$ and R$^4$ are independently hydrogen, C$_1$-C$_6$ alkyl, C$_1$-C$_6$ haloalkyl, C$_3$-C$_6$ alkenyl, C$_3$-C$_6$ haloalkenyl, C$_3$-C$_6$ alkynyl, formyl, C$_1$-C$_3$ alkylcarbonyl, C$_1$-C$_3$ haloalkylcarbonyl, C$_1$-C$_6$ alkoxycarbonyl, C$_1$-C$_6$ alkylcarbamyl, C$_1$-C$_6$ alkylsulfonyl, C$_1$-C$_6$ trialkylsilyl, C$_1$-C$_6$ dialkylphosphonyl, or R$^3$ and R$^4$ taken together with N is a 5- or 6-membered saturated ring, or R$^3$ and R$^4$ taken together represent =CR$^{3'}$(R$^{4'}$), wherein R$^{3'}$ and R$^{4'}$ are independently hydrogen, C$_1$-C$_6$ alkyl, C$_3$-C$_6$ alkenyl, C$_3$-C$_6$ alkynyl, C$_1$-C$_6$ alkoxy or $C_1$-$C_6$ alkylamino, or, $R^{3'}$ and $R^{4'}$ taken together with =C represent a 5- or 6-membered saturated ring;

A is A1, A2, A3, A4, A5, A6, A7, A8, A9, A10, A11, A12, A13, A14, A15, A16, A17, A18, A19, A20, A21, A22, A23, A24, A25, A26, A27, A28, A29, A30, A31, A32, A33, A34, A35, or A36;

$R^5$ is hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, OH, or CN;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments:

$R^1$ is $OR^{1'}$, wherein $R^{1'}$ is hydrogen, $C_1$-$C_8$ alkyl, or $C_7$-$C_{10}$ arylalkyl;

$R^2$ is halogen, $C_1$-$C_4$ alkyl, $C_1$-$C_4$ haloalkyl, $C_2$-$C_4$-alkenyl, $C_2$-$C_4$ haloalkenyl, $C_2$-$C_4$ alkynyl, $C_1$-$C_4$-alkoxy, $C_1$-$C_4$ haloalkoxy, $C_1$-$C_4$ alkylthio, or $C_1$-$C_4$ haloalkylthio;

$R^3$ and $R^4$ are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino;

A is A1, A2, A3, A7, A8, A9, A10, A11, A12, A13, A14, A15, A21, A22, A23, A24, A27, A28, A29, A30, A31, or A32;

$R^5$ is hydrogen, halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, or $C_2$-$C_4$ haloalkylamino;

$R^6$, $R^{6'}$, and $R^{6''}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, CN, or $NO_2$;

$R^7$ and $R^{7'}$ are independently hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, cyclopropyl, amino or $C_1$-$C_4$ alkylamino; and $R^8$ is hydrogen, $C_1$-$C_6$ alkyl, $C_1$-$C_4$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, $C_1$-$C_6$ alkoxycarbonyl, or $C_1$-$C_6$ alkylcarbamyl.

In some embodiments, $R^1$ is $OR^{1'}$, wherein $R^{1'}$ is hydrogen, $C_1$-$C_8$ alkyl, or $C_7$-$C_{10}$ arylalkyl.

In some embodiments, $R^2$ is halogen, $C_2$-$C_4$-alkenyl, $C_2$-$C_4$ haloalkenyl, or $C_1$-$C_4$-alkoxy.

In certain embodiments, $R^2$ is Cl, methoxy, vinyl, or 1-propenyl. In some embodiments, $R^3$ and $R^4$ are hydrogen.

In some embodiments, A is A1, A2, A3, A7, A8, A9, A10, A13, A14, or A15. In certain embodiments, A is A1, A2, A3, A13, A14, or A15. In certain embodiments, A is A15.

In some embodiments, $R^5$ is hydrogen or F. In certain embodiments, $R^5$ is F. In certain embodiments, $R^5$ is H.

In some embodiments, $R^6$ is hydrogen or F. In certain embodiments, $R^6$ is F. In certain embodiments, $R^6$ is H. In some embodiments, $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$. In certain embodiments, $R^6$, $R^{6'}$, and $R^{6''}$ are all hydrogen.

In certain embodiments, $R^2$ is Cl, methoxy, vinyl, or 1-propenyl; $R^3$ and $R^4$ are hydrogen; A is A15; $R^5$ is hydrogen or F; $R^6$ is hydrogen or F; and $R^{6''}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise a compound defined by Formula (III):

(III)

wherein

X is N or CY, wherein Y is hydrogen, halogen, $C_1$-$C_3$ alkyl, $C_1$-$C_3$ haloalkyl, $C_1$-$C_3$ alkoxy, $C_1$-$C_3$ haloalkoxy, $C_1$-$C_3$ alkylthio or $C_1$-$C_3$ haloalkylthio;

$R^1$ is $OR^{1'}$ or $NR^{1''}R^{1'''}$, wherein $R^{1'}$ is hydrogen, $C_1$-$C_8$ alkyl, or $C_7$-$C_{10}$ arylalkyl, and $R^{1''}$ and $R^{1'''}$ are independently hydrogen, $C_1$-$C_{12}$ alkyl, $C_3$-$C_{12}$ alkenyl, or $C_3$-$C_{12}$ alkynyl;

$R^2$ is halogen, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_1$-$C_4$ alkoxy, $C_1$-$C_4$ haloalkoxy, $C_1$-$C_4$ alkylthio, $C_1$-$C_4$ haloalkylthio, amino, $C_1$-$C_4$ alkylamino, $C_2$-$C_4$ haloalkylamino, formyl, $C_1$-$C_3$ alkylcarbonyl, $C_1$-$C_3$ haloalkylcarbonyl, cyano, or a group of the formula —$CR^{17}$=$CR^{18}$—$SiR^{19}R^{20}R^{21}$, wherein $R^{17}$ is hydrogen, F, or Cl; $R^{18}$ is hydrogen, F, Cl, $C_1$-$C_4$ alkyl, or $C_1$-$C_4$ haloalkyl; and $R^{19}$, $R^{20}$, and $R^{21}$ are independently $C_1$-$C_{10}$ alkyl, $C_3$-$C_6$ cycloalkyl, phenyl, substituted phenyl, $C_1$-$C_{10}$ alkoxy, or OH;

$R^3$ and $R^4$ are independently hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, $C_1$-$C_6$ dialkylphosphonyl, or $R^3$ and $R^4$ taken together with N is a 5- or 6-membered saturated ring, or $R^3$ and $R^4$ taken together represent =$CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino, or, $R^{3'}$ and $R^{4'}$ taken together with =C represent a 5- or 6-membered saturated ring;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino or $C_2$-$C_4$ haloalkylamino, OH, CN, or $NO_2$;

$R^7$ and $R^{7'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, $C_1$-$C_3$ alkylthio, $C_1$-$C_3$ haloalkylthio, amino, $C_1$-$C_4$ alkylamino, $C_2$-$C_4$ haloalkylamino, or phenyl; and $R^8$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, $C_1$-$C_6$ alkoxycarbonyl, $C_1$-$C_6$ alkylcarbamyl, $C_1$-$C_6$ alkylsulfonyl, $C_1$-$C_6$ trialkylsilyl, or phenyl;

or an agriculturally acceptable N-oxide or salt thereof.

In some embodiments:

X is N, CH, CF, CCl, or CBr;

$R^1$ is $OR^{1'}$, wherein $R^{1'}$ is hydrogen, $C_1$-$C_8$ alkyl, or $C_7$-$C_{10}$ arylalkyl;

$R^2$ is halogen, $C_1$-$C_4$ alkyl, $C_1$-$C_4$ haloalkyl, $C_2$-$C_4$-alkenyl, $C_2$-$C_4$ haloalkenyl, $C_2$-$C_4$ alkynyl, $C_1$-$C_4$-alkoxy, $C_1$-$C_4$ haloalkoxy, $C_1$-$C_4$ alkylthio, or $C_1$-$C_4$ haloalkylthio;

$R^3$ and $R^4$ are hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, formyl, $C_1$-$C_3$ alkylcarbonyl, $C_1$-$C_3$ haloalkylcarbonyl, or $R^3$ and $R^4$ taken together represent $=CR^{3'}(R^{4'})$, wherein $R^{3'}$ and $R^{4'}$ are independently hydrogen, $C_1$-$C_6$ alkyl, $C_3$-$C_6$ alkenyl, $C_3$-$C_6$ alkynyl, $C_1$-$C_6$ alkoxy or $C_1$-$C_6$ alkylamino;

$R^6$ and $R^{6'}$ are independently hydrogen, halogen, $C_1$-$C_4$ alkyl, $C_1$-$C_4$ haloalkyl, cyclopropyl, halocyclopropyl, $C_2$-$C_4$ alkenyl, $C_2$-$C_4$ haloalkenyl, $C_2$-$C_4$ alkynyl, $C_1$-$C_3$ alkoxy, $C_1$-$C_3$ haloalkoxy, CN, or $NO_2$;

$R^7$ and $R^{7'}$ are independently hydrogen, halogen, $C_1$-$C_4$ alkyl, $C_1$-$C_4$ haloalkyl, $C_1$-$C_3$ alkoxy, $C_1$-$C_3$ haloalkoxy, $C_1$-$C_3$ alkylthio, cyclopropyl, amino or $C_1$-$C_4$ alkylamino; and $R^8$ is hydrogen, $C_1$-$C_6$ alkyl, $C_1$-$C_4$ haloalkyl, $C_3$-$C_6$ alkenyl, $C_3$-$C_6$ haloalkenyl, formyl, $C_1$-$C_3$ alkylcarbonyl, $C_1$-$C_3$ haloalkylcarbonyl, $C_1$-$C_6$ alkoxycarbonyl, or $C_1$-$C_6$ alkylcarbamyl.

In some embodiments, X is N, CH or CF. In some embodiments, X is N. In some embodiments, X is CH. In some embodiments, X is CF. In other embodiments, X is C—$CH_3$.

In some embodiments, $R^2$ is halogen, $C_2$-$C_4$-alkenyl, $C_2$-$C_4$ haloalkenyl, or $C_1$-$C_4$-alkoxy.

In certain embodiments, $R^2$ is Cl, methoxy, vinyl, or 1-propenyl. In some embodiments, $R^3$ and $R^4$ are hydrogen.

In some embodiments, $R^6$ is hydrogen or F. In certain embodiments, $R^6$ is F. In certain embodiments, $R^6$ is H. In some embodiments, $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$. In certain embodiments, $R^6$ and $R^{6'}$ are both hydrogen.

In certain embodiments, $R^7$ and $R^{7'}$ are both hydrogen.

In certain embodiments, $R^6$, $R^{6'}$, $R^7$, and $R^{7'}$ are all hydrogen.

In certain embodiments, X is CF, $R^1$ is $OR^{1'}$, wherein $R^{1'}$ is hydrogen, $C_1$-$C_8$ alkyl, or $C_7$-$C_{10}$ arylalkyl; $R^2$ is Cl, methoxy, vinyl, or 1-propenyl; $R^3$ and $R^4$ are hydrogen; $R^6$ is hydrogen or F; and $R^{6'}$ is hydrogen, halogen, $C_1$-$C_4$ alkyl, $C_1$-$C_4$ haloalkyl, cyclopropyl, $C_2$-$C_4$ alkynyl, CN, or $NO_2$.

In certain embodiments, the pyridine carboxylic acid herbicide can comprise one of Compounds 1-24, the structures of which are shown in the table below.

| Compound No. | Structure |
|---|---|
| 1 | 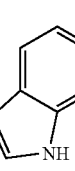 |
| 2 | 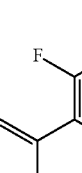 |
| 3 | 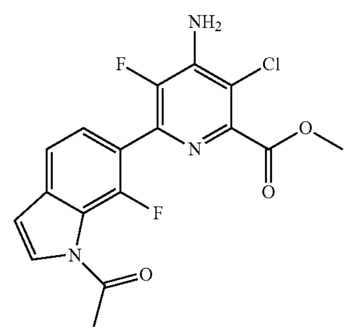 [SMILES: COC(=O)c1nc(-c2ccc3ccn(C(C)=O)c3c2F)c(F)c(N)c1Cl] |
| 4 | 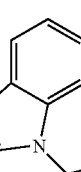 |
| 5 | 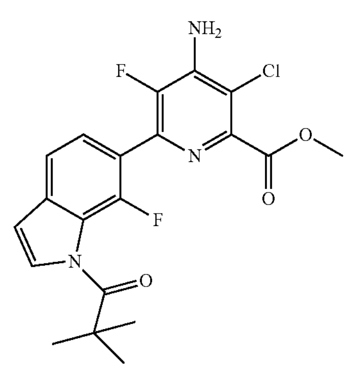 [SMILES: COC(=O)c1nc(-c2ccc3ccn(C(=O)C(C)(C)C)c3c2F)c(F)c(N)c1Cl] |

| Compound No. | Structure |
|---|---|
| 6 | 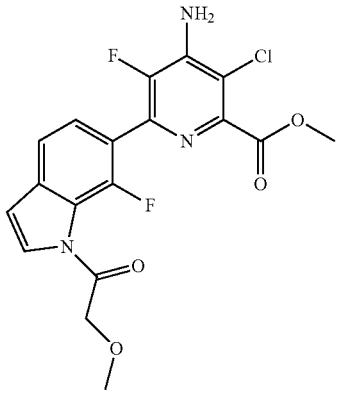 [SMILES: COCC(=O)n1ccc2ccc(-c3nc(C(=O)OC)c(Cl)c(N)c3F)c(F)c21] |
| 7 | 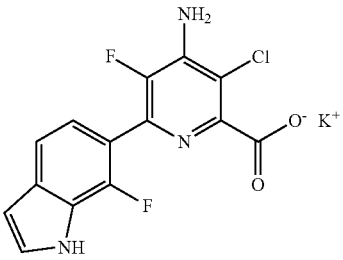 [SMILES: Nc1c(F)c(-c2ccc3cc[nH]c3c2F)nc(C(=O)[O-])c1Cl ; [K+]] |
| 8 | 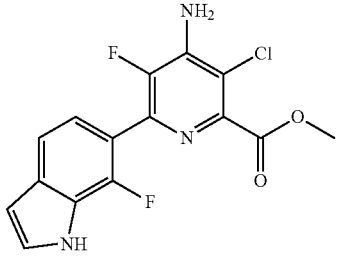 [SMILES: COC(=O)c1nc(-c2ccc3cc[nH]c3c2F)c(F)c(N)c1Cl] |
| 9 | 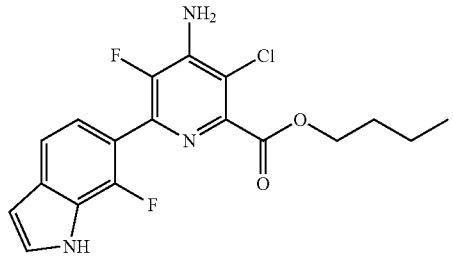 [SMILES: CCCCOC(=O)c1nc(-c2ccc3cc[nH]c3c2F)c(F)c(N)c1Cl] |
| 10 | 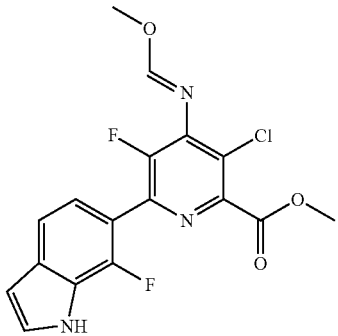 [SMILES: CO/C=N/c1c(F)c(-c2ccc3cc[nH]c3c2F)nc(C(=O)OC)c1Cl] |
| Compound No. | Structure |
|---|---|
| 11 | 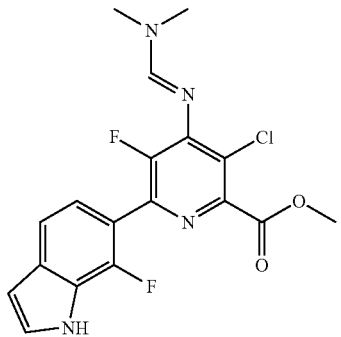 [SMILES: COC(=O)c1nc(-c2ccc3cc[nH]c3c2F)c(F)c(/N=C/N(C)C)c1Cl] |
| 12 | 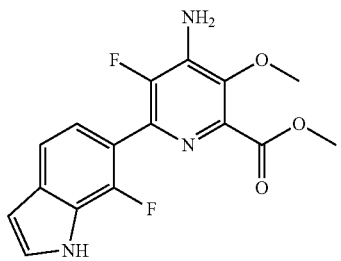 [SMILES: COC(=O)c1nc(-c2ccc3cc[nH]c3c2F)c(F)c(N)c1OC] |
| 13 | 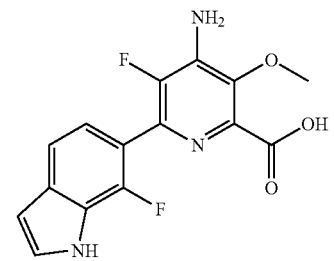 [SMILES: COc1c(C(=O)O)nc(-c2ccc3cc[nH]c3c2F)c(F)c1N] |
| 14 | 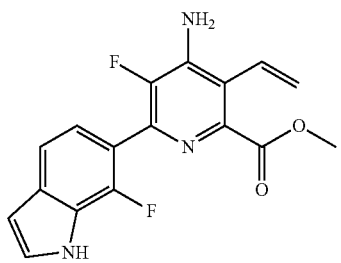 [SMILES: C=Cc1c(C(=O)OC)nc(-c2ccc3cc[nH]c3c2F)c(F)c1N] |
| 15 | 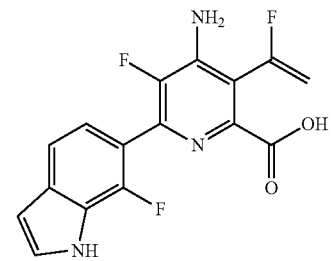 [SMILES: C=C(F)c1c(C(=O)O)nc(-c2ccc3cc[nH]c3c2F)c(F)c1N] |

| Compound No. | Structure |
|---|---|
| 16 | 4-amino-3-chloro-6-(7-fluoro-1H-indol-6-yl)picolinic acid |
| 17 | 4-amino-3-chloro-5-fluoro-6-(7-fluoro-1H-indol-5-yl)picolinic acid |
| 18 | 4-amino-3-chloro-5-fluoro-6-(1H-indol-6-yl)picolinic acid |
| 19 | 4-amino-3-chloro-5-fluoro-6-(benzo[d]thiazol-5-yl)picolinic acid |
| 20 | methyl 4-amino-3-chloro-5-fluoro-6-(benzo[b]thiophen-6-yl)picolinate |
| 21 | 6-amino-5-methoxy-2-(benzo[b]thiophen-6-yl)pyrimidine-4-carboxylic acid |
| 22 | 4-amino-3-chloro-5-fluoro-6-(benzofuran-6-yl)picolinic acid |
| 23 | methyl 4-amino-3-chloro-5-fluoro-6-(benzo[d]thiazol-6-yl)picolinate |
| 24 | methyl 6-amino-5-methoxy-2-(7-fluorobenzofuran-6-yl)pyrimidine-4-carboxylate |

In certain embodiments, the pyridine carboxylic acid herbicide can comprise 4-amino-3-chloro-5-fluoro-6-(7-fluoro-1H-indol-6-yl) picolinic acid, or an agriculturally acceptable N-oxide, salt, or ester thereof.

In some embodiments, the pyridine carboxylic acid herbicide can be provided as an agriculturally acceptable salt. Exemplary agriculturally acceptable salts of the pyridine carboxylic acid herbicides of Formula (I) include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, olamine salts, diglycolamine salts, choline salts, and quaternary ammonium salts such as those represented by the formula $R^9R^{10}R^{11}R^{12}N^+$ and wherein $R^9$, $R^{10}$, $R^{11}$ and $R^{12}$ (e.g., $R^9$—$R^{12}$) each independently can represent hydrogen, $C_1$-$C_{10}$ alkyl, $C_2$-$C_8$ alkenyl, $C_2$-$C_8$ alkynyl, $C_1$-$C_8$ alkoxy, $C_1$-$C_8$ alkylthio, or aryl groups, provided that $R^9$-$R^{12}$ are sterically compatible.

In some embodiments, the pyridine carboxylic acid herbicide can be provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl, butoxyethyl esters, substituted or unsubstituted aryl esters, orthoesters, substituted or unsubstituted alkylaryl esters, and substituted or unsubstituted arylalkyl esters. In some embodiments, the ester can comprise a $C_1$-$C_8$ alkyl ester, wherein the $C_1$-$C_8$ alkyl group is optionally substituted with one or more moieties selected from the group consisting of cyano, $C_2$-$C_8$ alkoxy, and $C_2$-$C_8$ alkylsulfonyl. For example, the ester can comprise a methyl, —$CH_2CN$, —$CH_2OCH_3$, —$CH_2OCH_2CH_2OCH_3$, or —$CH_2CH_2SO_2CH_3$ ester.

The ester can also be an acetal (e.g., a cyclic acetal) formed by protection of the carbonyl group in the pyridine carboxylic acid herbicides described above (e.g., by Formula (I)). For example, the pyridine carboxylic acid herbicides described above can be reacted with a suitable diol (e.g., a diol such as ethane-1,2-diol or butane-2,3-diol, for example, using standard protecting group chemistry, such as taught in Greene, et al., Protective Groups in Organic Synthesis, John Wiley and Sons, Fourth Edition, 2007, hereby incorporated by reference) to form a cyclic acetal. In one embodiment, the ester can be a cyclic acetal defined by the structure below, where $R^2$, $R^3$, $R^4$, X, and A are as described above.

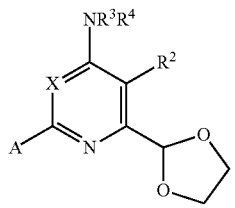

In some embodiments, the ester can comprise a substituted or unsubstituted benzyl ester. In some embodiments, the ester can comprise a benzyl ester optionally substituted with one or more moieties selected from the group consisting of halogen, $C_1$-$C_2$ alkyl, $C_1$-$C_2$ haloalkyl, and combinations thereof. In some embodiments, the ester can comprise a methyl ester.

The pyridine carboxylic acid herbicide, or an agriculturally acceptable N-oxide, salt, or ester thereof, can be applied to vegetation or an area adjacent the vegetation or applied to soil or water to prevent the emergence or growth of vegetation in an amount sufficient to induce a herbicidal effect. In some embodiments, the pyridine carboxylic acid herbicide, or an agriculturally acceptable N-oxide, salt, or ester thereof, is applied to vegetation or an area adjacent the vegetation or applied to soil or water to prevent the emergence or growth of vegetation in an amount of 0.1 grams of acid equivalent per hectare (g ae/ha) or greater (e.g., 0.2 g ae/ha or greater, 0.3 g ae/ha or greater, 0.4 g ae/ha or greater, 0.5 g ae/ha or greater, 0.6 g ae/ha or greater, 0.7 g ae/ha or greater, 0.8 g ae/ha or greater, 0.9 g ae/ha or greater, 1 g ae/ha or greater, 1.1 g ae/ha or greater, 1.2 g ae/ha or greater, 1.3 g ae/ha or greater, 1.4 g ae/ha or greater, 1.5 g ae/ha or greater, 1.6 g ae/ha or greater, 1.7 g ae/ha or greater, 1.8 g ae/ha or greater, 1.9 g ae/ha or greater, 2 g ae/ha or greater, 2.25 g ae/ha or greater, 2.5 g ae/ha or greater, 2.75 g ae/ha or greater, 3 g ae/ha or greater, 4 g ae/ha or greater, 5 g ae/ha or greater, 6 g ae/ha or greater, 7 g ae/ha or greater, 8 g ae/ha or greater, 9 g ae/ha or greater, 10 g ae/ha or greater, 11 g ae/ha or greater, 12 g ae/ha or greater, 13 g ae/ha or greater, 14 g ae/ha or greater, 15 g ae/ha or greater, 16 g ae/ha or greater, 17 g ae/ha or greater, 18 g ae/ha or greater, 19 g ae/ha or greater, 20 g ae/ha or greater, 21 g ae/ha or greater, 22 g ae/ha or greater, 23 g ae/ha or greater, 24 g ae/ha or greater, 25 g ae/ha or greater, 26 g ae/ha or greater, 27 g ae/ha or greater, 28 g ae/ha or greater, 29 g ae/ha or greater, 30 g ae/ha or greater, 31 g ae/ha or greater, 32 g ae/ha or greater, 33 g ae/ha or greater, 34 g ae/ha or greater, 35 g ae/ha or greater, 36 g ae/ha or greater, 37 g ae/ha or greater, 38 g ae/ha or greater, 39 g ae/ha or greater, 40 g ae/ha or greater, 41 g ae/ha or greater, 42 g ae/ha or greater, 43 g ae/ha or greater, 44 g ae/ha or greater, 45 g ae/ha or greater, 46 g ae/ha or greater, 47 g ae/ha or greater, 48 g ae/ha or greater, 49 g ae/ha or greater, 50 g ae/ha or greater, 55 g ae/ha or greater, 60 g ae/ha or greater, 65 g ae/ha or greater, 70 g ae/ha or greater, 75 g ae/ha or greater, 80 g ae/ha or greater, 85 g ae/ha or greater, 90 g ae/ha or greater, 95 g ae/ha or greater, 100 g ae/ha or greater, 110 g ae/ha or greater, 120 g ae/ha or greater, 130 g ae/ha or greater, 140 g ae/ha or greater, 150 g ae/ha or greater, 160 g ae/ha or greater, 170 g ae/ha or greater, 180 g ae/ha or greater, 190 g ae/ha or greater, 200 g ae/ha or greater, 210 g ae/ha or greater, 220 g ae/ha or greater, 230 g ae/ha or greater, 240 g ae/ha or greater, 250 g ae/ha or greater, 260 g ae/ha or greater, 270 g ae/ha or greater, 280 g ae/ha or greater, or 290 g ae/ha or greater). In some embodiments, the pyridine carboxylic acid herbicide, or an agriculturally acceptable N-oxide, salt, or ester thereof, is applied to vegetation or an area adjacent the vegetation or applied to soil or water to prevent the emergence or growth of vegetation in an amount of 300 g ae/ha or less (e.g., 290 g ae/ha or less, 280 g ae/ha or less, 270 g ae/ha or less, 260 g ae/ha or less, 250 g ae/ha or less, 240 g ae/ha or less, 230 g ae/ha or less, 220 g ae/ha or less, 210 g ae/ha or less, 200 g ae/ha or less, 190 g ae/ha or less, 180 g ae/ha or less, 170 g ae/ha or less, 160 g ae/ha or less, 150 g ae/ha or less, 140 g ae/ha or less, 130 g ae/ha or less, 120 g ae/ha or less, 110 g ae/ha or less, 100 g ae/ha or less, 95 g ae/ha or less, 90 g ae/ha or less, 85 g ae/ha or less, 80 g ae/ha or less, 75 g ae/ha or less, 70 g ae/ha or less, 65 g ae/ha or less, 60 g ae/ha or less, 55 g ae/ha or less, 50 g ae/ha or less, 49 g ae/ha or less, 48 g ae/ha or less, 47 g ae/ha or less, 46 g ae/ha or less, 45 g ae/ha or less, 44 g ae/ha or less, 43 g ae/ha or less, 42 g ae/ha or less, 41 g ae/ha or less, 40 g ae/ha or less, 39 g ae/ha or less, 38 g ae/ha or less, 37 g ae/ha or less, 36 g ae/ha or less, 35 g ae/ha or less, 34 g ae/ha or less, 33 g ae/ha or less, 32 g ae/ha or less, 31 g ae/ha or less, 30 g ae/ha or less, 29 g ae/ha or less, 28 g ae/ha or less, 27 g ae/ha or less, 26 g ae/ha or less, 25 g ae/ha or less, 24 g ae/ha or less, 23 g ae/ha or less, 22 g ae/ha or less, 21 g ae/ha or less, 20 g ae/ha or less, 19 g ae/ha or less, 18 g ae/ha or less, 17 g ae/ha or less, 16 g ae/ha or less, 15 g ae/ha or less, 14 g ae/ha or less, 13 g ae/ha or less, 12 g ae/ha or less, 11 g ae/ha or less, 10 g ae/ha or less, 9 g ae/ha or less, 8 g ae/ha or less, 7 g ae/ha or less, 6 g ae/ha or less, 5 g ae/ha or less, 4 g ae/ha or less, 3 g ae/ha or less, 2.75 g ae/ha or less, 2.5 g ae/ha or less, 2.25 g ae/ha or less, 2 g ae/ha or less, 1.9 g ae/ha or less, 1.8 g ae/ha or less, 1.7 g ae/ha or less, 1.6 g ae/ha or less, 1.5 g ae/ha or less, 1.4 g ae/ha or less, 1.3 g ae/ha or less, 1.2 g ae/ha or less, 1.1 g ae/ha or less, 1 g ae/ha or less, 0.9 g ae/ha or less, 0.8 g ae/ha or less, 0.7 g ae/ha or less, 0.6 g ae/ha or less, 0.5 g ae/ha or less, 0.4 g ae/ha or less, 0.3 g ae/ha or less, or 0.2 g ae/ha or less).

The pyridine carboxylic acid herbicide, or an agriculturally acceptable N-oxide, salt, or ester thereof, can be applied to vegetation or an area adjacent the vegetation or applied to soil or water to prevent the emergence or growth of vegetation in an amount ranging from any of the minimum values described above to any of the maximum values described above. In some embodiments, the pyridine carboxylic acid herbicide, or an agriculturally acceptable N-oxide, salt, or ester thereof, is applied to vegetation or an area adjacent the vegetation or applied to soil or water to prevent the emergence or growth of vegetation in an amount of from 0.1-300 g ae/ha (e.g., from 0.5-300 g ae/ha, from 0.1-5 g ae/ha, from 0.5-5 g ae/ha, from 2.5-40 g ae/ha, from 0.1-40 g ae/ha, from 0.5-40 g ae/ha, from 0.1-2.5 g ae/ha, from 0.5-2.5 g ae/ha, from 2-150 g ae/ha, from 5-75 g ae/ha, from 5-40 g ae/ha, from 5-30 g ae/ha, from 30-40 g ae/ha, or from 5-15 g ae/ha). In some embodiments, the pyridine carboxylic acid herbicide, or an agriculturally acceptable N-oxide, salt, or ester thereof, is applied in an amount from 5-40 g ae/ha. In some embodiments, the pyridine carboxylic acid herbicide, or an agriculturally acceptable N-oxide, salt, or ester thereof, is applied in an amount from 5-15 g ae/ha.

Photosystem II Inhibitors

In addition the pyridine carboxylic acid herbicide or agriculturally acceptable N-oxide, salt or ester thereof, the compositions can include a photosystem II inhibitor. Photosystem II inhibitors inhibit photosynthesis by binding to the photosystem II complex in the chloroplast. Examples of photosystem II inhibitors include triazine herbicides, triazinone herbicides, nitrile herbicides, benzothiadiazinone herbicides, and urea herbicides. In some embodiments, the photosystem II inhibitor can comprise a nitrile herbicide. In some embodiments, the photosystem II inhibitor can comprise a benzothiadiazinone herbicide. In some embodiments, the photosystem II inhibitor can comprise a urea herbicide. In some embodiments, the photosystem II inhibitor can comprise a triazinone herbicide. In some embodiments, the photosystem II inhibitor can comprise a triazine herbicide.

In some embodiments, the composition can include a photosystem II inhibitor selected from the group consisting of ametridione, ametryn, amibuzin, anisuron, atraton, atrazine, aziprotryne, bentazone, benzthiazuron, bromobonil, bromofenoxim, bromoxynil, buturon, buthiuron, chlorazine, chlorotoluron, chloroxynil, chlorbromuron, chloreturon, chloroxuron, cumyluron, cyanazine, cyprazine, cyanatryn, cycluron, daimuron, desmetryn, dimethametryn, dichloralurea, difenoxuron, dimefuron, dipropetryn, diuron, eglinazine, ethiozin, ethidimuron, fucaojing, fenuron, fluometuron, fluothiuron, hexazinone, ipazine, ioxynil, isoproturon, isomethiozin, iodobonil, isonoruron, isouron, linuorn, mesoprazine, metamitron, methabenzthiazuron, methometon, methoprotryn, methiuron, methyldymron, metobenzuron, metobromuron, metoxuron, metribuzin, monolinuron, monuron, monisouron, noruron, neburon, procyazine, proglinazine, propazine, prometon, prometryn, pyraclonil, parafluron, phenobenzuron, sebuthylazine, simazine, secbumeton, simeton, simetryn, terbuthylazine, trietazine, triaziflam, trihydroxytriazine, tebuthiuron, terbumeton, terbutryn, trifludimoxazin, tetrafluron, thidiazuron, thiazafluron, agriculturally acceptable salts and esters thereof, and combinations thereof.

Bromoxynil

In certain embodiments, the photosystem II inhibitor can comprise bromoxynil or an agriculturally acceptable salt or ester thereof. Bromoxynil, shown below, is a nitrile herbicide that provides broad-spectrum control of many annual broad-leaved weeds in cereals, ryegrass-seed crops, turfs, and non-crop land. Bromoxynil, as well as methods of preparing bromoxynil, are known in the art. Its herbicidal activity is described, for example, in The Pesticide Manual, Sixteenth Edition, 2012.

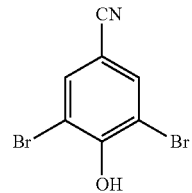 [SMILES: N#Cc1cc(Br)c(O)c(Br)c1]

In some embodiments, bromoxynil can be provided as an agriculturally acceptable salt or ester of bromoxynil. Exemplary agriculturally acceptable salts and esters of bromoxynil include, but are not limited to, bromoxynil butyrate, bromoxynil heptanoate, bromoxynil octanoate, and bromoxynil-potassium.

Bromoxynil or agriculturally acceptable salts or esters thereof are or have been commercially available, for example, under the trademarks BROMOTRIL® (by Makhteshim-Agan), BROMOXONE® (by Sundat), MUTINY® (by Barclay), BROMINAL® (by Bayer CropScience), BUCTRIL® (by Bayer CropScience), BROMOX® (by Dow AgroSciences), BROMOXAN® (by Dow AgroSciences), and EMBLEM® (by Nufarm Europe).

The photosystem II inhibitor (e.g., bromoxynil) or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the photosystem II inhibitor or agriculturally acceptable salt or ester thereof is applied to vegetation or an area adjacent the vegetation or applied to soil or water to prevent the emergence or growth of vegetation in an amount of 5 grams of active ingredient per hectare (g ai/ha) or greater (e.g., 10 g ai/ha or greater, 15 g ai/ha or greater, 20 g ai/ha or greater, 25 g ai/ha or greater, 30 g ai/ha or greater, 35 g ai/ha or greater, 40 g ai/ha or greater, 45 g ai/ha or greater, 50 g ai/ha or greater, 55 g ai/ha or greater, 60 g ai/ha or greater, 65 g ai/ha or greater, 70 g ai/ha or greater, 75 g ai/ha or greater, 80 g ai/ha or greater, 85 g ai/ha or greater, 90 g ai/ha or greater, 95 g ai/ha or greater, 100 g ai/ha or greater, 110 g ai/ha or greater, 120 g ai/ha or greater, 130 g ai/ha or greater, 140 g ai/ha or greater, 150 g ai/ha or greater, 160 g ai/ha or greater, 170 g ai/ha or greater, 180 g ai/ha or greater, 190 g ai/ha or greater, 200 g ai/ha or greater, 210 g ai/ha or greater, 220 g ai/ha or greater, 230 g ai/ha or greater, 240 g ai/ha or greater, 250 g ai/ha or greater, 260 g ai/ha or greater, 270 g ai/ha or greater, 280 g ai/ha or greater, 290 g ai/ha or greater, 300 g ai/ha or greater, 310 g ai/ha or greater, 320 g ai/ha or greater, 330 g ai/ha or greater, 340 g ai/ha or greater, 350 g ai/ha or greater, 360 g ai/ha or greater, 370 g ai/ha or greater, 380 g ai/ha or greater, 390 g ai/ha or greater, 400 g ai/ha or greater, 420 g ai/ha or greater, 440 g ai/ha or greater, 460 g ai/ha or greater, 480 g ai/ha or greater, 500 g ai/ha or greater, 520 g ai/ha or greater, 540 g ai/ha or greater, 560 g ai/ha or greater, 580 g ai/ha or greater, 600 g ai/ha or greater, 625 g ai/ha or greater, 650 g ai/ha or greater, 675 g ai/ha or greater, 700 g ai/ha or greater, 725 g ai/ha or greater, 750 g ai/ha or greater, 775 g ai/ha or greater, 800 g ai/ha or greater, 825 g ai/ha or greater, 850 g ai/ha or greater, 875 g ai/ha or greater, 900 g ai/ha or greater, 925 g ai/ha or greater, 950 g ai/ha or greater, 975 g ai/ha or greater, 1000 g ai/ha or greater, 1100 g ai/ha or greater, 1200 g ai/ha or greater, 1300 g ai/ha or greater, 1400 g ai/ha or greater, 1500 g ai/ha or greater, 1600 g ai/ha or greater, 1700 g ai/ha or greater, 1800 g ai/ha or greater, 1900 g ai/ha or greater, 2000 g ai/ha or greater, 2100 g ai/ha or greater, 2200 g ai/ha or greater, 2300 g ai/ha or greater, 2400 g ai/ha or greater, 2500 g ai/ha or greater, 2600 g ai/ha or greater, 2700 g ai/ha or greater, 2800 g ai/ha or greater, 2900 g ai/ha or greater, 3000 g ai/ha or greater, 3100 g ai/ha or greater, 3200 g ai/ha or greater, 3300 g ai/ha or greater, 3400 g ai/ha or greater, 3500 g ai/ha or greater, 3600 g ai/ha or greater, 3700 g ai/ha or greater, 3800 g ai/ha or greater, or 3900 g ai/ha or greater).

In some embodiments, the photosystem II inhibitor (e.g., bromoxynil) or agriculturally acceptable salt or ester thereof is applied to vegetation or an area adjacent the vegetation or applied to soil or water to prevent the emergence or growth of vegetation in an amount of 4000 g ai/ha or less (e.g., 3900 g ai/ha or less, 3800 g ai/ha or less, 3700 g ai/ha or less, 3600 g ai/ha or less, 3500 g ai/ha or less, 3400 g ai/ha or less, 3300 g ai/ha or less, 3200 g ai/ha or less, 3100 g ai/ha or less, 3000 g ai/ha or less, 2900 g ai/ha or less, 2800 g ai/ha or less, 2700 g ai/ha or less, 2600 g ai/ha or less, 2500 g ai/ha or less, 2400 g ai/ha or less, 2300 g ai/ha or less, 2200 g ai/ha or less, 2100 g ai/ha or less, 2000 g ai/ha or less, 1900 g ai/ha or less, 1800 g ai/ha or less, 1700 g ai/ha or less, 1600 g ai/ha or less, 1500 g ai/ha or less, 1400 g ai/ha or less, 1300 g ai/ha or less, 1200 g ai/ha or less, 1100 g ai/ha or less, 1000 g ai/ha or less, 975 g ai/ha or less, 950 g ai/ha or less, 925 g ai/ha or less, 900 g ai/ha or less, 875 g ai/ha or less, 850 g ai/ha or less, 825 g ai/ha or less, 800 g ai/ha or less, 775 g ai/ha or less, 750 g ai/ha or less, 725 g ai/ha or less, 700 g ai/ha or less, 675 g ai/ha or less, 650 g ai/ha or less, 625 g ai/ha or less, 600 g ai/ha or less, 580 g ai/ha or less, 560 g ai/ha or less, 540 g ai/ha or less, 520 g ai/ha or less, 500 g ai/ha or less, 480 g ai/ha or less, 460 g ai/ha or less, 440 g ai/ha or less, 420 g ai/ha or less, 400 g ai/ha or less, 390 g ai/ha or less, 380 g ai/ha or less, 370 g ai/ha or less, 360 g ai/ha or less, 350 g ai/ha or less, 340 g ai/ha or less, 330 g ai/ha or less, 320 g ai/ha or less, 310 g ai/ha or less, 300 g ai/ha or less, 290 g ai/ha or less, 280 g ai/ha or less, 270 g ai/ha or less, 260 g ai/ha or less, 250 g ai/ha or less, 240 g ai/ha or less, 230 g ai/ha or less, 220 g ai/ha or less, 210 g ai/ha or less, 200 g ai/ha or less, 190 g ai/ha or less, 180 g ai/ha or less, 170 g ai/ha or less, 160 g ai/ha or less, 150 g ai/ha or less, 140 g ai/ha or less, 130 g ai/ha or less, 120 g ai/ha or less, 110 g ai/ha or less, 100 g ai/ha or less, 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, 55 g ai/ha or less, 50 g ai/ha or less, 45 g ai/ha or less, 40 g ai/ha or less, 35 g ai/ha or less, 30 g ai/ha or less, 25 g ai/ha or less, 20 g ai/ha or less, 15 g ai/ha or less, or 10 g ai/ha or less).

The photosystem II inhibitor (e.g., bromoxynil) or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the photosystem II inhibitor (e.g., bromoxynil) or agriculturally acceptable salt or ester thereof is applied to vegetation or an area adjacent the vegetation or applied to soil or water to prevent the emergence or growth of vegetation in an amount of from 5-4000 g ai/ha (e.g., from 5-3000 g ai/ha, from 3000-4000 g ai/ha, from 5-2900 g ai/ha, from 5-2800 g ai/ha, from 5-2700 g ai/ha, from 5-2600 g ai/ha, from 5-2500 g ai/ha, from 5-2400 g ai/ha, from 5-2300 g ai/ha, from 5-2200 g ai/ha, from 5-2100 g ai/ha, from 5-2000 g ai/ha, from 5-1800 g ai/ha, from 5-1600 g ai/ha, from 5-1400 g ai/ha, from 5-1200 g ai/ha, from 5-1000 g ai/ha, from 5-750 g ai/ha, from 750-1000 g ai/ha, from 5-700 g ai/ha, from 5-650 g ai/ha, from 5-600 g ai/ha, from 5-560 g ai/ha, from 5-500 g ai/ha, from 5-460 g ai/ha, from 5-400 g ai/ha, from 5-460 g ai/ha, from 5-400 g ai/ha, from 5-360 g ai/ha, from 5-300 g ai/ha, from 5-280 g ai/ha, from 5-260 g ai/ha, from 5-240 g ai/ha, from 5-220 g ai/ha, from 5-200 g ai/ha, from 5-180 g ai/ha, from 5-160 g ai/ha, from 5-140 g ai/ha, from 5-120 g ai/ha, from 5-100 g ai/ha, from 5-90 g ai/ha, from 5-80 g ai/ha, from 5-70 g ai/ha, from 5-60 g ai/ha, from 5-50 g ai/ha, from 5-40 g ai/ha, from 5-30 g ai/ha, from 5-20 g ai/ha, from 5-10 g ai/ha, from 10-4000 g ai/ha, from 10-3000 g ai/ha, from 10-2000 g ai/ha, from 20-4000 g ai/ha, from 20-3000 g ai/ha, from 20-2000 g ai/ha, from 20-1500 g ai/ha, from 30-4000 g ai/ha, from 30-3000 g ai/ha, from 30-2000 g ai/ha, from 50-4000 g ai/ha, from 50-3000 g ai/ha, from 50-2000 g ai/ha, from 50-1500 g ai/ha, from 70-4000 g ai/ha, from 70-3000 g ai/ha, from 70-2500 g ai/ha, from 70-2000 g ai/ha, from 70-1500 g ai/ha, from 100-3000 g ai/ha, from 100-2500 g ai/ha, from 100-2000 g ai/ha, from 10-560 g ai/ha, from 20-500 g ai/ha, from 30-460 g ai/ha, from 40-400 g ai/ha, from 50-360 g ai/ha, from 60-300 g ai/ha, from 70-280 g ai/ha, from 70-100 g ai/ha, from 70-140 g ai/ha, from 100-140 g ai/ha, from 100-280 g ai/ha, or from 140-280 g ai/ha). In certain embodiments, the photosystem II inhibitor (e.g., bromoxynil) or agriculturally acceptable salt or ester thereof is applied to vegetation or an area adjacent the vegetation or applied to soil or water to prevent the emergence or growth of vegetation in an amount of from 30-1000 g ai/ha. In certain embodiments, the photosystem II inhibitor (e.g., bromoxynil) or agriculturally acceptable salt or ester thereof is applied to vegetation or an area adjacent the vegetation or applied to soil or water to prevent the emergence or growth of vegetation in an amount of from 30-300 g ai/ha.

Bentazon

In certain embodiments, the photosystem II inhibitor can comprise bentazon or an agriculturally acceptable salt or ester thereof. Bentazon or bentazone, shown below, is a benzothiadiazinone herbicide that provides control of broadleaf and sedge weeds in broadleaf and grass crops. It is also known as bentazone. Bentazon, as well as methods of preparing bentazon, are known in the art. Its herbicidal activity is described, for example, in *The Pesticide Manual*, Fifteenth Edition, 2009.

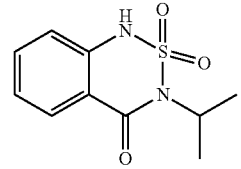 [SMILES: CC(C)N1C(=O)c2ccccc2NS1(=O)=O]

In some embodiments, bentazon can be provided as an agriculturally acceptable salt of bentazon. An exemplary agriculturally acceptable salt of bentazon is bentazon-sodium.

Bentazon or agriculturally acceptable salts thereof are or have been commercially available, for example, under the trademark BASAGRAN® (by BASF), SUNTAZONE® (by Sundat (S) Pte. Ltd), ADAGIO® (by Phyteurop), BANIR® (by Sipcam Agro S/A), BAZANO® (by Herbos d. d.), BLAST® (by Sipcam S.p.A., Vapco), ERBAZONE® (by Siapa S.r.l.), PILARTAZONE® (by Pilaquim); TROY® (by Interfarm (UK) Ltd); and YONA® (by Dogal).

The photosystem II inhibitor (e.g., bentazon) or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the photosystem II inhibitor or agriculturally acceptable salt or ester thereof is applied to vegetation or an area adjacent the vegetation or applied to soil or water to prevent the emergence or growth of vegetation in an amount of 30 grams active ingredient per hectare (g ai/ha) or greater (e.g., 35 g ai/ha or greater, 40 g ai/ha or greater, 45 g ai/ha or greater, 50 g ai/ha or greater, 55 g ai/ha or greater, 60 g ai/ha or greater, 65 g ai/ha or greater, 70 g ai/ha or greater, 75 g ai/ha or greater, 80 g ai/ha or greater, 85 g ai/ha or greater, 90 g ai/ha or greater, 100 g ai/ha or greater, 110 g ai/ha or greater, 120 g ai/ha or greater, 130 g ai/ha or greater, 140 g ai/ha or greater, 150 g ai/ha or greater, 160 g ai/ha or greater, 170 g ai/ha or greater, 180 g ai/ha or greater, 190 g ai/ha or greater, 200 g ai/ha or greater, 210 g ai/ha or greater, 220 g ai/ha or greater, 230 g ai/ha or greater, 240 g ai/ha or greater, 250 g ai/ha or greater, 260 g ai/ha or greater, 270 g ai/ha or greater, 280 g ai/ha or greater, 290 g ai/ha or greater, 300 g ai/ha or greater, 310 g ai/ha or greater, 320 g ai/ha or greater, 330 g ai/ha or greater, 340 g ai/ha or greater, 350 g ai/ha or greater, 360 g ai/ha or greater, 370 g ai/ha or greater, 380 g ai/ha or greater, 390 g ai/ha or greater, 400 g ai/ha or greater, 420 g ai/ha or greater, 440 g ai/ha or greater, 460 g ai/ha or greater, 480 g ai/ha or greater, 500 g ai/ha or greater, 525 g ai/ha or greater, 550 g ai/ha or greater, 575 g ai/ha or greater, 600 g ai/ha or greater, 625 g ai/ha or greater, 650 g ai/ha or greater, 675 g ai/ha or greater, 700 g ai/ha or greater, 725 g ai/ha or greater, 750 g ai/ha or greater, 775 g ai/ha or greater, 800 g ai/ha or greater, 825 g ai/ha or greater, 850 g ai/ha or greater, 875 g ai/ha or greater, 900 g ai/ha or greater, 925 g ai/ha or greater, 950 g ai/ha or greater, 975 g ai/ha or greater, 1000 g ai/ha or greater, 1200 g ai/ha or greater, 1400 g ai/ha or greater, 1600 g ai/ha or greater, 1800 g ai/ha or greater, 2000 g ai/ha or greater, 2200 g ai/ha or greater, or 2230 g ai/ha or greater).

In some embodiments, the photosystem II inhibitor (e.g., bentazon) or agriculturally acceptable salt or ester thereof is applied to vegetation or an area adjacent the vegetation or applied to soil or water to prevent the emergence or growth of vegetation in an amount of 2240 g ai/ha or less (e.g., 2200 g ai/ha or less, 2000 g ai/ha or less, 1800 g ai/ha or less, 1600 g ai/ha or less, 1400 g ai/ha or less, 1200 g ai/ha or less, 1000 g ai/ha or less, 975 g ai/ha or less, 950 g ai/ha or less, 925 g ai/ha or less, 900 g ai/ha or less, 875 g ai/ha or less, 850 g ai/ha or less, 825 g ai/ha or less, 800 g ai/ha or less, 775 g ai/ha or less, 750 g ai/ha or less, 725 g ai/ha or less, 700 g ai/ha or less, 675 g ai/ha or less, 650 g ai/ha or less, 625 g ai/ha or less, 600 g ai/ha or less, 575 g ai/ha or less, 550 g ai/ha or less, 525 g ai/ha or less, 500 g ai/ha or less, 480 g ai/ha or less, 460 g ai/ha or less, 440 g ai/ha or less, 420 g ai/ha or less, 400 g ai/ha or less, 390 g ai/ha or less, 380 g ai/ha or less, 370 g ai/ha or less, 360 g ai/ha or less, 350 g ai/ha or less, 340 g ai/ha or less, 330 g ai/ha or less, 320 g ai/ha or less, 310 g ai/ha or less, 300 g ai/ha or less, 290 g ai/ha or less, 280 g ai/ha or less, 270 g ai/ha or less, 260 g ai/ha or less, 250 g ai/ha or less, 240 g ai/ha or less, 230 g ai/ha or less, 220 g ai/ha or less, 210 g ai/ha or less, 200 g ai/ha or less, 190 g ai/ha or less, 180 g ai/ha or less, 170 g ai/ha or less, 160 g ai/ha or less, 150 g ai/ha or less, 140 g ai/ha or less, 130 g ai/ha or less, 120 g ai/ha or less, 110 g ai/ha or less, 100 g ai/ha or less, 95 g ai/ha or less, 90 g ai/ha or less, 85 g ai/ha or less, 80 g ai/ha or less, 75 g ai/ha or less, 70 g ai/ha or less, 65 g ai/ha or less, 60 g ai/ha or less, 55 g ai/ha or less, 50 g ai/ha or less, 45 g ai/ha or less, 40 g ai/ha or less, or 35 g ai/ha or less).

The photosystem II inhibitor (e.g., bentazon) or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the photosystem II inhibitor (e.g., bentazon) or agriculturally acceptable salt or ester thereof is applied to vegetation or an area adjacent the vegetation or applied to soil or water to prevent the emergence or growth of vegetation in an amount of from 30-2240 g ai/ha (e.g., from 30-1000 g ai/ha, from 1000-2240 g ai/ha, from 30-2000 g ai/ha, from 40-2000 g ai/ha, from 40-1800 g ai/ha, from 40-1600 g ai/ha, from 40-1500 g ai/ha, from 50-2240 g ai/ha, from 50-2000 g ai/ha, from 50-1800 g ai/ha, from 50-1600 g ai/ha, from 50-1500 g ai/ha, from 55-2240 g ai/ha, from 55-2000 g ai/ha, from 55-1800 g ai/ha, from 55-1600 g ai/ha, from 55-1500 g ai/ha, from 60-2240 g ai/ha, from 60-2000 g ai/ha, from 60-1800 g ai/ha, from 60-1600 g ai/ha, from 60-1500 g ai/ha, from 60-1400 g ai/ha, from 60-1300 g ai/ha, from 60-1200 g ai/ha, from 60-1100 g ai/ha, from 60-1000 g ai/ha, from 60-800 g ai/ha, from 60-600 g ai/ha, from 60-400 g ai/ha, from 60-200 g ai/ha, from 60-150 g ai/ha, from 60-100 g ai/ha, from 60-90 g ai/ha, from 60-85 g ai/ha, from 60-80 g ai/ha, from 50-1000 g ai/ha, from 50-800 g ai/ha, from 50-600 g ai/ha, from 50-500 g ai/ha, from 50-250 g ai/ha, from 100-1000 g ai/ha, from 100-1500 g ai/ha, or from 100-2200 g ai/ha). In certain embodiments, the photosystem II inhibitor (e.g., bentazon) or agriculturally acceptable salt or ester thereof is applied to vegetation or an area adjacent the vegetation or applied to soil or water to prevent the emergence or growth of vegetation in an amount of from 60-900 g ai/ha.

Isoproturon

In certain embodiments, the photosystem II inhibitor can comprise isoproturon. Isoproturon, shown below, is a urea herbicide that provides pre- and post-emergence control of annual grasses and many broadleaf weeds in spring and winter wheat, spring and winter barley, winter rye, and triticale. Isoproturon, as well as methods of preparing isoproturon, are known in the art. Its herbicidal activity is described, for example, in *The Pesticide Manual*, Fifteenth Edition, 2009.

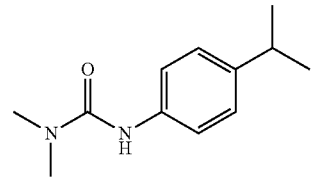

Isoproturon has been commercially available, for example, under the trademark ALON® (by CGNS Ltd), ARELON® (by Nufarm España S.A.), DHANULON® (by Dhanuka Group), ISOGUARD® (by Chiltem Farm Chemicals Ltd, Gharda Chemicals Ltd), ISORON® (by Hermoo Belgium N.V.), NARILON® (by Nagarjuna Agrichem Ltd), PASPORT® (by RPG Life Sciences Ltd), PROTON® (by Devidayal Agro Chemicals); TOLKAN® and STRONG® (by Bayer CropScience), TOTALON® (by Crop Health Products Ltd) and TURONEX® (by Agriphar S.A.).

The photosystem II inhibitor (e.g., isoproturon) or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the photosystem II inhibitor (e.g., isoproturon) or agriculturally acceptable salt or ester thereof is applied to vegetation or an area adjacent the vegetation or applied to soil or water to prevent the emergence or growth of vegetation in an amount of 75 grams active ingredient per hectare (g ai/ha) or greater (e.g., 80 g ai/ha or greater, 85 g ai/ha or greater, 90 g ai/ha or greater, 100 g ai/ha or greater, 105 g ai/ha or greater, 110 g ai/ha or greater, 115 g ai/ha or greater, 120 g ai/ha or greater, 125 g ai/ha or greater, 130 g ai/ha or greater, 135 g ai/ha or greater, 140 g ai/ha or greater, 145 g ai/ha or greater, 150 g ai/ha or greater, 160 g ai/ha or greater, 170 g ai/ha or greater, 180 g ai/ha or greater, 190 g ai/ha or greater, 200 g ai/ha or greater, 210 g ai/ha or greater, 220 g ai/ha or greater, 230 g ai/ha or greater, 240 g ai/ha or greater, 250 g ai/ha or greater, 260 g ai/ha or greater, 270 g ai/ha or greater, 280 g ai/ha or greater, 290 g ai/ha or greater, 300 g ai/ha or greater, 310 g ai/ha or greater, 320 g ai/ha or greater, 330 g ai/ha or greater, 340 g ai/ha or greater, 350 g ai/ha or greater, 360 g ai/ha or greater, 370 g ai/ha or greater, 380 g ai/ha or greater, 390 g ai/ha or greater, 400 g ai/ha or greater, 420 g ai/ha or greater, 440 g ai/ha or greater, 460 g ai/ha or greater, 480 g ai/ha or greater, 500 g ai/ha or greater, 525 g ai/ha or greater, 550 g ai/ha or greater, 575 g ai/ha or greater, 600 g ai/ha or greater, 625 g ai/ha or greater, 650 g ai/ha or greater, 675 g ai/ha or greater, 700 g ai/ha or greater, 725 g ai/ha or greater, 750 g ai/ha or greater, 775 g ai/ha or greater, 800 g ai/ha or greater, 825 g ai/ha or greater, 850 g ai/ha or greater, 875 g ai/ha or greater, 900 g ai/ha or greater, 925 g ai/ha or greater, 950 g ai/ha or greater, 975 g ai/ha or greater, 1000 g ai/ha or greater, 1100 g ai/ha or greater, 1200 g ai/ha or greater, 1300 g ai/ha or greater, or 1400 g ai/ha or greater).

In some embodiments, the photosystem II inhibitor (e.g., isoproturon) or agriculturally acceptable salt or ester thereof is applied to vegetation or an area adjacent the vegetation or applied to soil or water to prevent the emergence or growth of vegetation in an amount of 1500 g ai/ha or less (e.g., 1400 g ai/ha or less, 1200 g ai/ha or less, 1100 g ai/ha or less, 1000 g ai/ha or less, 975 g ai/ha or less, 950 g ai/ha or less, 925 g ai/ha or less, 900 g ai/ha or less, 875 g ai/ha or less, 850 g ai/ha or less, 825 g ai/ha or less, 800 g ai/ha or less, 775 g ai/ha or less, 750 g ai/ha or less, 725 g ai/ha or less, 700 g ai/ha or less, 675 g ai/ha or less, 650 g ai/ha or less, 625 g ai/ha or less, 600 g ai/ha or less, 575 g ai/ha or less, 550 g ai/ha or less, 525 g ai/ha or less, 500 g ai/ha or less, 480 g ai/ha or less, 460 g ai/ha or less, 440 g ai/ha or less, 420 g ai/ha or less, 400 g ai/ha or less, 390 g ai/ha or less, 380 g ai/ha or less, 370 g ai/ha or less, 360 g ai/ha or less, 350 g ai/ha or less, 340 g ai/ha or less, 330 g ai/ha or less, 320 g ai/ha or less, 310 g ai/ha or less, 300 g ai/ha or less, 290 g ai/ha or less, 280 g ai/ha or less, 270 g ai/ha or less, 260 g ai/ha or less, 250 g ai/ha or less, 240 g ai/ha or less, 230 g ai/ha or less, 220 g ai/ha or less, 210 g ai/ha or less, 200 g ai/ha or less, 190 g ai/ha or less, 180 g ai/ha or less, 170 g ai/ha or less, 160 g ai/ha or less, 150 g ai/ha or less, 145 g ai/ha or less, 140 g ai/ha or less, 135 g ai/ha or less, 130 g ai/ha or less, 125 g ai/ha or less, 120 g ai/ha or less, 115 g ai/ha or less, 110 g ai/ha or less, 105 g ai/ha or less, 100 g ai/ha or less, 95 g ai/ha or less, 90 g ai/ha or less, 85 g ai/ha or less, or 80 g ai/ha or less).

The photosystem II inhibitor (e.g., isoproturon) or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the photosystem II inhibitor (e.g., isoproturon) or agriculturally acceptable salt or ester thereof is applied to vegetation or an area adjacent the vegetation or applied to soil or water to prevent the emergence or growth of vegetation in an amount of from 75-1500 g ai/ha (e.g., from 75-750 g ai/ha, from 750-1500 g ai/ha, from 75-1400 g ai/ha, from 75-1300 g ai/ha, from 75-1200 g ai/ha, from 75-1000 g ai/ha, from 75-800 g ai/ha, from 100-1500 g ai/ha, from 100-1400 g ai/ha, from 100-1300 g ai/ha, from 100-1200 g ai/ha, from 100-1100 g ai/ha, from 100-1000 g ai/ha, from 125-1500 g ai/ha, from 125-1400 g ai/ha, from 125-1300 g ai/ha, from 125-1200 g ai/ha, from 125-1100 g ai/ha, from 125-1000 g ai/ha, from 125-900 g ai/ha, from 125-800 g ai/ha, from 125-750 g ai/ha, from 125-700 g ai/ha, from 125-700 g ai/ha, from 125-600 g ai/ha, from 125-500 g ai/ha, from 125-400 g ai/ha, from 125-300 g ai/ha, from 135-1500 g ai/ha, from 135-1400 g ai/ha, from 135-1300 g ai/ha, from 135-1200 g ai/ha, from 135-1100 g ai/ha, from 135-1000 g ai/ha, from 135-800 g ai/ha, from 135-600 g ai/ha, from 135-500 g ai/ha, from 135-400 g ai/ha, from 135-300 g ai/ha, from 135-200 g ai/ha, from 140-1200 g ai/ha, from 140-1000 g ai/ha, from 140-800 g ai/ha, or from 140-600 g ai/ha). In certain embodiments, the photosystem II inhibitor (e.g., isoproturon) or agriculturally acceptable salt or ester thereof is applied to vegetation or an area adjacent the vegetation or applied to soil or water to prevent the emergence or growth of vegetation in an amount of from 150-1000 g ai/ha.

Metribuzin

In certain embodiments, the photosystem II inhibitor can comprise metribuzin or an agriculturally acceptable salt of metribuzin. Metribuzin, shown below, is a triazinone herbicide that provides pre- and post-emergence control of annual grasses and many broadleaf weeds in soybeans, potatoes, tomatoes, sugar cane, alfalfa, asparagus, corn and cereals. Metribuzin, as well as methods of preparing metribuzin, are known in the art. Its herbicidal activity is described, for example, in *The Pesticide Manual*, Fifteenth Edition, 2009.

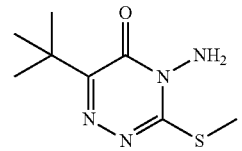

In some embodiments, metribuzin can be provided as an agriculturally acceptable salt of metribuzin.

Metribuzin or agriculturally acceptable salts thereof are or have been commercially available, for example, under the trademark ALISO® (by Cequisa), HILMETRI® (by Hindustan Insecticides Ltd), LEXONE® (by DuPont Crop Protection), MAJOR® (Crop Health), METIROC® (by Rocca), METRIZIN (by Hermoo Belgium N.V.), METROZIN® (by Mobedco), MISTRAL® (by Feinchemie Schwebda GmbH, Adama Agricultural Solutions), SENCOR® (by Bayer CropScience), SENTRY® (by Shenzhen Baocheng Chemical Industry Co. Ltd), SUBUZIN® (by Sundat (S) Ptd. Ltd), VAPCOR® (by Vapco), MAESTRO® (by Aako B.V.), and MASTER® (Aako B.V.).

The photosystem II inhibitor (e.g., metribuzin) or agriculturally acceptable salt or ester thereof can be applied to vegetation or an area adjacent the vegetation or applied to soil or water to prevent the emergence or growth of vegetation in an amount sufficient to induce a herbicidal effect.

In some embodiments, the photosystem II inhibitor (e.g., metribuzin) or agriculturally acceptable salt or ester thereof is applied to vegetation or an area adjacent the vegetation or applied to soil or water to prevent the emergence or growth of vegetation in an amount of 12.5 grams active ingredient per hectare (g ai/ha) or greater (e.g., 15 g ai/ha or greater, 20 g ai/ha or greater, 25 g ai/ha or greater, 30 g ai/ha or greater, 35 g ai/ha or greater, 40 g ai/ha or greater, 45 g ai/ha or greater, 50 g ai/ha or greater, 60 g ai/ha or greater, 70 g ai/ha or greater, 80 g ai/ha or greater, 90 g ai/ha or greater, 100 g ai/ha or greater, 120 g ai/ha or greater, 140 g ai/ha or greater, 160 g ai/ha or greater, 180 g ai/ha or greater, 200 g ai/ha or greater, 220 g ai/ha or greater, 240 g ai/ha or greater, 260 g ai/ha or greater, 280 g ai/ha or greater, 300 g ai/ha or greater, 320 g ai/ha or greater, 340 g ai/ha or greater, 360 g ai/ha or greater, 380 g ai/ha or greater, 400 g ai/ha or greater, 420 g ai/ha or greater, 440 g ai/ha or greater, 460 g ai/ha or greater, 480 g ai/ha or greater, 500 g ai/ha or greater, 525 g ai/ha or greater, 550 g ai/ha or greater, 575 g ai/ha or greater, 600 g ai/ha or greater, 625 g ai/ha or greater, 650 g ai/ha or greater, 675 g ai/ha or greater, 700 g ai/ha or greater, 725 g ai/ha or greater, 750 g ai/ha or greater, 800 g ai/ha or greater, 850 g ai/ha or greater, 900 g ai/ha or greater, 950 g ai/ha or greater, 1000 g ai/ha or greater, 1100 g ai/ha or greater, 1200 g ai/ha or greater, 1300 g ai/ha or greater, 1400 g ai/ha or greater, 1500 g ai/ha or greater, 1600 g ai/ha or greater, 1700 g ai/ha or greater, 1800 g ai/ha or greater, 1900 g ai/ha or greater, 2000 g ai/ha or greater, 2100 g ai/ha or greater, 2200 g ai/ha or greater, 2300 g ai/ha or greater, 2400 g ai/ha or greater, 2500 g ai/ha or greater, 2600 g ai/ha or greater, 2700 g ai/ha or greater, 2800 g ai/ha or greater, 2900 g ai/ha or greater, 3000 g ai/ha or greater, 3100 g ai/ha or greater, 3200 g ai/ha or greater, 3300 g ai/ha or greater, 3400 g ai/ha or greater, 3500 g ai/ha or greater, 3600 g ai/ha or greater, 3700 g ai/ha or greater, 3800 g ai/ha or greater, or 3900 g ai/ha or greater).

In some embodiments, the photosystem II inhibitor (e.g., metribuzin) or agriculturally acceptable salt or ester thereof is applied to vegetation or an area adjacent the vegetation or applied to soil or water to prevent the emergence or growth of vegetation in an amount of 4000 g ai/ha or less (e.g., 3900 g ai/ha or less, 3800 g ai/ha or less, 3700 g ai/ha or less, 3600 g ai/ha or less, 3500 g ai/ha or less, 3400 g ai/ha or less, 3300 g ai/ha or less, 3200 g ai/ha or less, 3100 g ai/ha or less, 3000 g ai/ha or less, 2900 g ai/ha or less, 2800 g ai/ha or less, 2700 g ai/ha or less, 2600 g ai/ha or less, 2500 g ai/ha or less, 2400 g ai/ha or less, 2300 g ai/ha or less, 2200 g ai/ha or less, 2100 g ai/ha or less, 2000 g ai/ha or less, 1900 g ai/ha or less, 1800 g ai/ha or less, 1700 g ai/ha or less, 1600 g ai/ha or less, 1500 g ai/ha or less, 1400 g ai/ha or less, 1300 g ai/ha or less, 1200 g ai/ha or less, 1100 g ai/ha or less, 1000 g ai/ha or less, 950 g ai/ha or less, 900 g ai/ha or less, 850 g ai/ha or less, 800 g ai/ha or less, 750 g ai/ha or less, 725 g ai/ha or less, 700 g ai/ha or less, 675 g ai/ha or less, 650 g ai/ha or less, 625 g ai/ha or less, 600 g ai/ha or less, 575 g ai/ha or less, 550 g ai/ha or less, 525 g ai/ha or less, 500 g ai/ha or less, 480 g ai/ha or less, 460 g ai/ha or less, 440 g ai/ha or less, 420 g ai/ha or less, 400 g ai/ha or less, 380 g ai/ha or less, 360 g ai/ha or less, 340 g ai/ha or less, 320 g ai/ha or less, 300 g ai/ha or less, 280 g ai/ha or less, 260 g ai/ha or less, 240 g ai/ha or less, 220 g ai/ha or less, 200 g ai/ha or less, 180 g ai/ha or less, 160 g ai/ha or less, 140 g ai/ha or less, 120 g ai/ha or less, 100 g ai/ha or less, 90 g ai/ha or less, 80 g ai/ha or less, 70 g ai/ha or less, 60 g ai/ha or less, 50 g ai/ha or less, 45 g ai/ha or less, 40 g ai/ha or less, 35 g ai/ha or less, 30 g ai/ha or less, 25 g ai/ha or less, 20 g ai/ha or less, or 15 g ai/ha or less).

The photosystem II inhibitor (e.g., metribuzin) or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the photosystem II inhibitor (e.g., metribuzin) or agriculturally acceptable salt or ester thereof is applied to vegetation or an area adjacent the vegetation or applied to soil or water to prevent the emergence or growth of vegetation in an amount of from 12.5-4000 g ai/ha (e.g., from 12.5-2000 g ai/ha, from 2000-4000 g ai/ha, from 12.5-3750 g ai/ha, from 12.5-3500 g ai/ha, from 12.5-3000 g ai/ha, from 12.5-2500 g ai/ha, from 12.5-2000 g ai/ha, from 15-4000 g ai/ha, from 15-3750 g ai/ha, from 15-3500 g ai/ha, from 15-3000 g ai/ha, from 15-2500 g ai/ha, from 15-2000 g ai/ha, from 20-4000 g ai/ha, from 20-3750 g ai/ha, from 20-3500 g ai/ha, from 20-3000 g ai/ha, from 20-2500 g ai/ha, from 20-2000 g ai/ha, from 20-1500 g ai/ha, from 20-1000 g ai/ha, from 20-900 g ai/ha, from 20-800 g ai/ha, from 20-700 g ai/ha, from 20-600 g ai/ha, from 20-500 g ai/ha, from 20-400 g ai/ha, from 20-300 g ai/ha, from 25-4000 g ai/ha, from 25-3750 g ai/ha, from 25-3500 g ai/ha, from 25-3000 g ai/ha, from 25-2500 g ai/ha, from 25-2000 g ai/ha, from 25-1500 g ai/ha, from 25-1000 g ai/ha, from 25-900 g ai/ha, from 25-800 g ai/ha, from 25-700 g ai/ha, from 25-600 g ai/ha, from 30-4000 g ai/ha, from 30-3000 g ai/ha, from 30-2000 g ai/ha, or from 30-1000 g ai/ha). In certain embodiments, the photosystem II inhibitor (e.g., metribuzin) or agriculturally acceptable salt or ester thereof is applied to vegetation or an area adjacent the vegetation or applied to soil or water to prevent the emergence or growth of vegetation in an amount of from 30-750 g ai/ha.

Atrazine

In certain embodiments, the photosystem II inhibitor can comprise atrazine or an agriculturally acceptable salt of atrazine. Atrazine, shown below, is a triazine herbicide that provides pre- and post-emergence control of annual broad-leaved weeds and annual grasses in corn, *sorghum*, sugar cane, pineapples, chemical fallow, grassland, macadamia nuts, conifers, and industrial weed control. Atrazine, as well as methods of preparing atrazine, are known in the art. Its herbicidal activity is described, for example, in *The Pesticide Manual*, Fifteenth Edition, 2009.

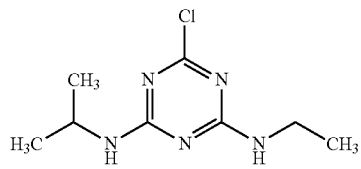

In some embodiments, atrazine can be provided as an agriculturally acceptable salt of atrazine.

Atrazine or agriculturally acceptable salts thereof are or have been commercially available, for example, under the trademark AATREX® (by Syngenta), ATRANEX® (by Adama Agricultural Solutions), ATRAPLEX® (by Ingenieria Industrial S.A. de C.V.), ATRATAF® (by Rallis India Ltd), ATRATYLONE® (by Agriphar S.A.), ATRAZILA® (by Shenzhen Baocheng Chemical Industry Co. Ltd), ATRAZOL® (by Sipcam S.p.A.), ATTACK® (by Devidayal Agro Chemicals), COYOTE® (by Milenia Agro Ciencias S.A.), DHANUZINE® (by Dhanuka Group), SANAZINE®

(by Dow AgroSciences), SURYA® (by Nagarjuna Agrichem Ltd), TRIAFLOW (by Inquiport, S.A.), ZEAZIN® S 40 (by Istrochem a.s.), and AKOZINE® (by Aako B.V.).

The photosystem II inhibitor (e.g., atrazine) or agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the photosystem II inhibitor (e.g., atrazine) or agriculturally acceptable salt or ester thereof is applied to vegetation or an area adjacent the vegetation or applied to soil or water to prevent the emergence or growth of vegetation in an amount of 225 grams active ingredient per hectare (g ai/ha) or greater (e.g., 230 g ai/ha or greater, 240 g ai/ha or greater, 250 g ai/ha or greater, 260 g ai/ha or greater, 270 g ai/ha or greater, 280 g ai/ha or greater, 290 g ai/ha or greater, 300 g ai/ha or greater, 310 g ai/ha or greater, 320 g ai/ha or greater, 330 g ai/ha or greater, 340 g ai/ha or greater, 350 g ai/ha or greater, 360 g ai/ha or greater, 370 g ai/ha or greater, 380 g ai/ha or greater, 390 g ai/ha or greater, 400 g ai/ha or greater, 420 g ai/ha or greater, 440 g ai/ha or greater, 460 g ai/ha or greater, 480 g ai/ha or greater, 500 g ai/ha or greater, 525 g ai/ha or greater, 550 g ai/ha or greater, 575 g ai/ha or greater, 600 g ai/ha or greater, 625 g ai/ha or greater, 650 g ai/ha or greater, 675 g ai/ha or greater, 700 g ai/ha or greater, 725 g ai/ha or greater, 750 g ai/ha or greater, 775 g ai/ha or greater, 800 g ai/ha or greater, 825 g ai/ha or greater, 850 g ai/ha or greater, 875 g ai/ha or greater, 900 g ai/ha or greater, 925 g ai/ha or greater, 950 g ai/ha or greater, 975 g ai/ha or greater, 1000 g ai/ha or greater, 1200 g ai/ha or greater, 1400 g ai/ha or greater, 1600 g ai/ha or greater, 1800 g ai/ha or greater, 2000 g ai/ha or greater, 2200 g ai/ha or greater, 2400 g ai/ha or greater, 2600 g ai/ha or greater, 2800 g ai/ha or greater, 3000 g ai/ha or greater, 3200 g ai/ha or greater, 3400 g ai/ha or greater, 3600 g ai/ha or greater, 3800 g ai/ha or greater, 4000 g ai/ha or greater, 4100 g ai/ha or greater, 4200 g ai/ha or greater, 4300 g ai/ha or greater, or 4400 g ai/ha or greater).

In some embodiments, the photosystem II inhibitor (e.g., atrazine) or agriculturally acceptable salt or ester thereof is applied to vegetation or an area adjacent the vegetation or applied to soil or water to prevent the emergence or growth of vegetation in an amount of 4400 g ai/ha or less (e.g., 4300 g ai/ha or less, 4200 g ai/ha or less, 4100 g ai/ha or less, 4000 g ai/ha or less, 3800 g ai/ha or less, 3600 g ai/ha or less, 3400 g ai/ha or less, 3200 g ai/ha or less, 3000 g ai/ha or less, 2800 g ai/ha or less, 2600 g ai/ha or less, 2400 g ai/ha or less, 2200 g ai/ha or less, 2000 g ai/ha or less, 1800 g ai/ha or less, 1600 g ai/ha or less, 1400 g ai/ha or less, 1200 g ai/ha or less, 1000 g ai/ha or less, 975 g ai/ha or less, 950 g ai/ha or less, 925 g ai/ha or less, 900 g ai/ha or less, 875 g ai/ha or less, 850 g ai/ha or less, 825 g ai/ha or less, 800 g ai/ha or less, 775 g ai/ha or less, 750 g ai/ha or less, 725 g ai/ha or less, 700 g ai/ha or less, 675 g ai/ha or less, 650 g ai/ha or less, 625 g ai/ha or less, 600 g ai/ha or less, 575 g ai/ha or less, 550 g ai/ha or less, 525 g ai/ha or less, 500 g ai/ha or less, 480 g ai/ha or less, 460 g ai/ha or less, 440 g ai/ha or less, 420 g ai/ha or less, 400 g ai/ha or less, 390 g ai/ha or less, 380 g ai/ha or less, 370 g ai/ha or less, 360 g ai/ha or less, 350 g ai/ha or less, 340 g ai/ha or less, 330 g ai/ha or less, 320 g ai/ha or less, 310 g ai/ha or less, 300 g ai/ha or less, 290 g ai/ha or less, 280 g ai/ha or less, 270 g ai/ha or less, 260 g ai/ha or less, 250 g ai/ha or less, 240 g ai/ha or less, or 230 g ai/ha or less).

The photosystem II inhibitor (e.g., atrazine) or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the photosystem II inhibitor (e.g., atrazine) or agriculturally acceptable salt or ester thereof is applied to vegetation or an area adjacent the vegetation or applied to soil or water to prevent the emergence or growth of vegetation in an amount of from 225-4400 g ai/ha (e.g., from 225-2000 g ai/ha, from 2000-4400 g ai/ha, from 225-1750 g ai/ha, from 225-1500 g ai/ha, from 225-1250 g ai/ha, from 225-1000 g ai/ha, from 225-750 g ai/ha, from 225-500 g ai/ha, from 225-450 g ai/ha, from 225-400 g ai/ha, from 250-4400 g ai/ha, from 250-4000 g ai/ha, from 250-3600 g ai/ha, from 250-3200 g ai/ha, from 250-2800 g ai/ha, from 250-2400 g ai/ha, from 250-2000 g ai/ha, from 250-1500 g ai/ha, from 250-1000 g ai/ha, from 250-750 g ai/ha, from 250-600 g ai/ha, from 250-500 g ai/ha, from 250-450 g ai/ha, from 250-400 g ai/ha, from 300-4400 g ai/ha, from 300-4000 g ai/ha, from 300-3600 g ai/ha, from 300-3200 g ai/ha, from 300-2800 g ai/ha, from 300-2400 g ai/ha, from 300-2000 g ai/ha, from 300-1500 g ai/ha, from 300-1000 g ai/ha, from 300-750 g ai/ha, from 30-500 g ai/ha, or from 300-400 g ai/ha). In certain embodiments, the photosystem II inhibitor (e.g., atrazine) or agriculturally acceptable salt or ester thereof is applied to vegetation or an area adjacent the vegetation or applied to soil or water to prevent the emergence or growth of vegetation in an amount of from 225-1000 g ai/ha.

II. Compositions

A. Herbicidal Mixtures or Combinations

The (a) pyridine carboxylic acid herbicide or an agriculturally acceptable N-oxide, salt, or ester thereof can be mixed with or applied in combination with (b) a photosystem II inhibitor, or an agriculturally acceptable salt or ester thereof. In some embodiments, (a) and (b) are used in an amount sufficient to induce a synergistic herbicidal effect while still showing good crop compatibility (i.e., their use in crops does not result in increased damage to crops when compared to the individual application of the herbicidal compounds (a) or (b)). As described in the *Herbicide Handbook* of the Weed Science Society of America, Tenth Edition, 2014, p. 487, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and Antagonistic Responses of Herbicide Combinations*, WEEDS 15, p. 22 (1967)

$$E = X * Y - \frac{X * Y}{100}$$

wherein

X=effect in percent using (a) a pyridine carboxylic acid herbicide or an agriculturally acceptable N-oxide, salt, or ester thereof at an application rate a;

Y=effect in percent using (b) a photosystem II inhibitor or an agriculturally acceptable salt or ester thereof at an application rate b;

E=expected effect (in %) of (a)+(b) at application rates a and b.

In Colby's equation, the value E corresponds to the effect (plant damage or injury) that is to be expected if the activity of the individual compounds is additive. If the observed effect is higher than the value E calculated according to the Colby equation, then a synergistic effect is present according to the Colby equation.

In some embodiments, the compositions and methods disclosed herein are synergistic as defined by the Colby equation. In some embodiments, the joint action of a pyridine carboxylic acid herbicide or an agriculturally acceptable N-oxide, salt, or ester thereof and a photosystem II inhibitor or an agriculturally acceptable salt or ester thereof results in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e., they effect damaging of undesired vegetation more quickly compared with application of the individual herbicides).

In some embodiments, the observed effect for undesired vegetation is at least 1%, at least 2%, at least 3%, at least 4%, at least 5%, at least 10%, at least 15%, at least 20%, or at least 25% greater than the effect (E) calculated according to the Colby equation (e.g., an observed effect of 96% would be 4% greater than an calculated effect (E) of 92%). In some embodiments, for undesired vegetation, the difference ($D_O$) between 100% and the observed effect is at least 5%, at least 10%, at least 15%, at least 20%, at least 25%, at least 30%, at least 35%, at least 40%, at least 45%, or at least 50% less than the difference ($D_E$) between 100% and the effect (E) calculated according to the Colby equation (e.g., an observed effect of 96% would produce a $D_O$ of 4%, a calculated effect (E) of 92% would produce a $D_E$ of 8%, and $D_O$ would be 50% less than or half of $D_E$).

In some embodiments, the weight ratio of (a) a pyridine carboxylic acid herbicide or an agriculturally acceptable N-oxide, salt, or ester thereof in g ae/ha to (b) a photosystem II inhibitor, or an agriculturally acceptable salt or ester thereof in g ai/ha that is sufficient to induce a synergistic herbicidal effect is 1:8000 or more (e.g., 1:7500 or more, 1:7000 or more, 1:6500 or more, 1:6000 or more, 1:5500 or more, 1:5000 or more, 1:4500 or more, 1:4000 or more, 1:3500 or more, 1:3000 or more, 1:2500 or more, 1:2000 or more, 1:1500 or more, 1:1000 or more, 1:900 or more, 1:800 or more, 1:700 or more, 1:600 or more, 1:500 or more, 1:400 or more, 1:300 or more, 1:200 or more, 1:100 or more, 1:90 or more, 1:80 or more, 1:70 or more, 1:60 or more, 1:50 or more, 1:45 or more, 1:40 or more, 1:35 or more, 1:30 or more, 1:25 or more, 1:20 or more, 1:15 or more, 1:10 or more, 1:9 or more, 1:8 or more, 1:7 or more, 1:6 or more, 1:5 or more, 1:4.75 or more, 1:4.5 or more, 1:4.25 or more, 1:4 or more, 1:3.75 or more, 1:3.5 or more, 1:3.25 or more, 1:3 or more, 1:2.75 or more, 1:2.5 or more, 1:2.25 or more, 1:2 or more, 1:1.9 or more, 1:1.8 or more, 1:1.7 or more, 1:1.6 or more, 1:1.5 or more, 1:1.4 or more, 1:1.3 or more, 1:1.2 or more, 1:1.1 or more, 1:1 or more, 1.1:1 or more, 1.2:1 or more, 1.3:1 or more, 1.4:1 or more, 1.5:1 or more, 1.6:1 or more, 1.7:1 or more, 1.8:1 or more, 1.9:1 or more, 2:1 or more, 2.25:1 or more, 2.5:1 or more, 2.75:1 or more, 3:1 or more, 3.25:1 or more, 3.5:1 or more, 3.75:1 or more, 4:1 or more, 4.25:1 or more, 4.5:1 or more, 4.75:1 or more, 5:1 or more, 6:1 or more, 7:1 or more, 8:1 or more, 9:1 or more, 10:1 or more, 15:1 or more, 20:1 or more, 25:1 or more, 30:1 or more, 35:1 or more, 40:1 or more, 45:1 or more, 50:1 or more, or 55:1 or more).

In some embodiments, the weight ratio of (a) a pyridine carboxylic acid herbicide or an agriculturally acceptable N-oxide, salt, or ester thereof in g ae/ha to (b) a photosystem II inhibitor, or an agriculturally acceptable salt or ester thereof in g ai/ha that is sufficient to induce a synergistic herbicidal effect is 60:1 or less (e.g., 55:1 or less, 50:1 or less, 45:1 or less, 40:1 or less, 35:1 or less, 30:1 or less, 25:1 or less, 20:1 or less, 15:1 or less, 10:1 or less, 9:1 or less, 8:1 or less, 7:1 or less, 6:1 or less, 5:1 or less, 4.75:1 or less, 4.5:1 or less, 4.25:1 or less, 4:1 or less, 3.75:1 or less, 3.5:1 or less, 3.25:1 or less, 3:1 or less, 2.75:1 or less, 2.5:1 or less, 2.25:1 or less, 2:1 or less, 1.9:1 or less, 1.8:1 or less, 1.7:1 or less, 1.6:1 or less, 1.5:1 or less, 1.4:1 or less, 1.3:1 or less, 1.2:1 or less, 1.1:1 or less, 1:1 or less, 1:1.1 or less, 1:1.2 or less, 1:1.3 or less, 1:1.4 or less, 1:1.5 or less, 1:1.6 or less, 1:1.7 or less, 1:1.8 or less, 1:1.9 or less, 1:2 or less, 1:2.25 or less, 1:2.5 or less, 1:2.75 or less, 1:3 or less, 1:3.25 or less, 1:3.5 or less, 1:3.75 or less, 1:4 or less, 1:4.25 or less, 1:4.5 or less, 1:4.75 or less, 1:5 or less, 1:6 or less, 1:7 or less, 1:8 or less, 1:9 or less, 1:10 or less, 1:15 or less, 1:20 or less, 1:25 or less, 1:30 or less, 1:35 or less, 1:40 or less, 1:45 or less, 1:50 or less, 1:60 or less, 1:70 or less, 1:80 or less, 1:90 or less, 1:100 or less, 1:200 or less, 1:300 or less, 1:400 or less, 1:500 or less, 1:600 or less, 1:700 or less, 1:800 or less, 1:900 or less, 1:1000 or less, 1:1500 or less, 1:2000 or less, 1:2500 or less, 1:3000 or less, 1:3500 or less, 1:4000 or less, 1:4500 or less, 1:5000 or less, 1:5500 or less, 1:6000 or less, 1:6500 or less, 1:7000 or less, 1:7500 or less).

The weight ratio of (a) a pyridine carboxylic acid herbicide or an agriculturally acceptable N-oxide, salt, or ester thereof in g ae/ha to (b) a photosystem II inhibitor, or an agriculturally acceptable salt or ester thereof in g ai/ha that is sufficient to induce a synergistic herbicidal effect can range from any of the minimum ratios described above to any of the maximum values described above. For example, in some embodiments, the weight ratio of (a) a pyridine carboxylic acid herbicide or an agriculturally acceptable N-oxide, salt, or ester thereof in g ae/ha to (b) a photosystem II inhibitor, or an agriculturally acceptable salt or ester thereof in g ai/ha that is sufficient to induce a synergistic herbicidal effect is from 1:8000 to 60:1 (e.g., 1:8000 to 4.9:1, from 1:700 to 4.8:1, from 1:6000 to 4.7:1, from 1:5000 to 4.6:1, from 1:4000 to 4.5:1, from 1:3000 to 4.4:1, from 1:2000 to 4.3:1, from 1:1000 to 4.2:1, from 1:1000 to 60:1, from 1:1000 to 20:1, from 1:1000 to 5:1, from 1:900 to 10:1, from 1:800 to 9:1, from 1:700 to 8:1, from 1:600 to 8:1, from 1:500 to 8:1, from 1:400 to 8:1, from 1:300 to 8:1, from 1:900 to 50:1, from 1:800 to 40:1, from 1:700 to 30:1, from 1:600 to 20:1, from 1:500 to 15:1, from 1:400 to 10:1, from 1:300 to 9:1, from 1:200 to 8:1, from 1:100 to 7:1, from 1:50 to 6:1, from 1:50 to 4.5:1, from 1:40 to 5:1, from 1:900 to 4.9:1, from 1:800 to 4.8:1, from 1:700 to 4.7:1, from 1:600 to 4.6:1, from 1:500 to 4.5:1, from 1:400 to 4.4:1, from 1:300 to 4.3:1, from 1:200 to 4.2:1, from 1:100 to 4.1:1, from 1:40 to 4:1, from 1:30 to 4:1, from 1:30 to 3.5:1, from 1:20 to 3:1, from 1:10 to 2:1, from 1:5 to 5:1, from 1:4 to 4:1, from 1:3 to 3:1, from 1:2 to 2:1 from 1:1.9 to 1.9:1, from 1:1.8 to 1.8:1, from 1:1.7 to 1.7:1, from 1:1.6 to 1.6:1, from 1:1.5 to 1.5:1, from 1:1.4 to 1.4:1, from 1:1.3 to 1.3:1, from 1:1.2 to 1.2:1, from 1:1.1 to 1.1:1, from 1:35 to 1:1, from 1:34 to 1:1, from 1:33 to 1:1, from 1:32 to 1:1, from 1:31 to 1:1, from 1:30 to 1:1, from 1:29 to 1:1, from 1:28 to 1:1, from 1:27 to 1:1, from 1:26 to 1:1, from 1:25 to 1:1, from 1:24 to 1:1, from 1:23 to 1:1, from 1:22 to 1:1, from 1:21 to 1:1, from 1:20 to 1:1, from 1:19 to 1:1, from 1:18 to 1:1, from 1:17 to 1:1, from 1:16 to 1:1, from 1:15 to 1:1, from 1:14 to 1:1, from 1:13 to 1:1, from 1:12 to 1:1, from 1:11 to 1:1, from 1:10 to 1:1, from 1:9 to 1:1, from 1:8 to 1:1, from 1:7 to 1:1, from 1:6 to 1:1, from 1:5 to 1:1, from 1:4 to 1:1, from 1:3 to 1:1, from 1:2 to 1:1, from 1:1.9 to 1:1, from 1:1.8 to 1:1, from 1:1.7 to 1:1, from 1:1.6 to 1:1, from 1:1.5 to 1:1, from 1:1.4 to 1:1, from 1:1.3 to 1:1, from 1:1.2 to 1:1, or from 1:1.1 to 1:1). In certain embodiments, the weight ratio of (a) a pyridine carboxylic acid herbicide or an agriculturally acceptable N-oxide, salt, or ester thereof in g ae/ha to (b) a photosystem II inhibitor, or an agriculturally acceptable salt or ester thereof in g ai/ha that is sufficient to induce a synergistic herbicidal effect is from 1:32 to 1:3.5 (e.g., from 1:16 to 1:7, from 1:32 to 3.5:1, or from 1:16 to 1:1).

In some embodiments, the active ingredients in the compositions disclosed herein consist of (a) a pyridine carboxylic acid herbicide or an agriculturally acceptable N-oxide, salt, or ester thereof and (b) a photosystem II inhibitor, or an agriculturally acceptable salt or ester thereof.

B. Formulations

The present disclosure also relates to formulations of the compositions and methods disclosed herein. In some embodiments, the formulation can be in the form of a single package formulation including both (a) a pyridine carboxylic acid herbicide or an agriculturally acceptable N-oxide, salt, or ester thereof and (b) a photosystem II inhibitor, or an agriculturally acceptable salt or ester thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a) and (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, self-emulsifying formulations, pastes, dusts, and materials for spreading or granules.

In some embodiments, (a) a pyridine carboxylic acid herbicide or an agriculturally acceptable N-oxide, salt, or ester thereof and/or (b) a photosystem II inhibitor, or an agriculturally acceptable salt or ester thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the pyridine carboxylic acid herbicide or agriculturally acceptable N-oxide, salt, or ester thereof. In some embodiments, the additive is premixed with the photosystem II inhibitor or agriculturally acceptable salt or ester thereof.

C. Other Actives

In some embodiments, the additive is an additional pesticide. For example, the compositions described herein can be applied in conjunction with one or more additional herbicides to control undesirable vegetation. The composition can be formulated with the one or more additional herbicides, tank mixed with the one or more additional herbicides, or applied sequentially with the one or more additional herbicides. Exemplary additional herbicides include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, amicarbazone, amidosulfuron, aminocyclopyrachlor, 4-aminopicolinic acid based herbicides, such as halauxifen, halauxifen-methyl, 4-amino-3-chloro-6-(4-chloro-2-fluoro-3-methoxyphenyl)-5-fluoro-2-pyridinecarboxylic acis, benzyl 4-amino-3-chloro-6-(4-chloro-2-fluoro-3-methoxyphenyl)-5-fluoro-2-pyridinecarboxylate, and those described in U.S. Pat. Nos. 7,314,849 and 7,432,227 to Balko, et al., aminopyralid, amiprofos-methyl, amitrole, ammonium sulfamate, anilofos, asulam, azafenidin, barban, BCPC, beflubutamid, benazolin, bencarbazone, benfluralin, benfuresate, bensulide, benthiocarb, benzadox, benzfendizone, benzipram, benzobicyclon, benzofenap, benzofluor, benzoylprop, bicyclopyrone, bifenox, bilanafos, borax, bromacil, bromobutide, brompyrazon, butachlor, butafenacil, butamifos, butenachlor, buthidazole, butralin, butroxydim, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorbufam, chlorfenac, chlorfenprop, chlorflurazole, chlorflurenol, chloridazon, chlorimuron, chlornitrofen, chloropon, chlorpropham, chlorsulfuron, chlorthal, chlorthiamid, cinidon-ethyl, cinmethylin, cisanilide, clacyfos, clethodim, cliodinate, clodinafop-propargyl, clofop, clomazone, clomeprop, cloprop, cloproxydim, clopyralid, cloransulammethyl, CMA, copper sulfate, CPMF, CPPC, credazine, cresol, cycloate, cyclopyrimorate, cyclosulfamuron, cycloxydim, cyhalofop-butyl, cyperquat, cyprazole, cypromid, dalapon, dazomet, delachlor, desmedipham, di-allate, dicamba, dichlobenil, dichlormate, dichlorprop, dichlorprop-P, diclofop-methyl, diclosulam, diethamquat, diethatyl, difenopenten, difenzoquat, diflufenican, diflufenzopyr, dimepiperate, dimethachlor, dimethenamid, dimethenamid-P, dimexano, dimidazon, dinitramine, dinofenate, dinoprop, dinosam, dinoseb, dinoterb, diphenamid, diquat, disul, dithiopyr, DMPA, DNOC, DSMA, EBEP, endothal, epronaz, EPTC, erbon, esprocarb, ethalfluralin, ethbenzamide, ethametsulfuron, ethiolate, ethobenzamid, etobenzamid, ethofumesate, ethoxyfen, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenquinotrione, fenteracol, fenthiaprop, fentrazamide, ferrous sulfate, flamprop, flamprop-M, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluorodifen, fluoroglycofen, fluoromidine, fluoronitrofen, flupoxam, flupropacil, flupropanate, flupyrsulfuron, fluridone, flurochloridone, fluroxypyr, fluroxypyr-meptyl, flurtamone, fluthiacet, fomesafen, foramsulfuron, fosamine, fumiclorac, furyloxyfen, glufosinate, glufosinate-ammonium, glufosinate-P-ammonium, glyphosate salts and esters, halosafen, haloxydine, hexachloroacetone, hexaflurate, imazamethabenz, imazapic, imazapyr, imazaquin, indaziflam, indanofan, iodomethane, iodosulfuron, iodosulfuron-ethyl-sodium, iofensulfuron, ipfencarbazone, iprymidam, isocarbamid, isocil, isopolinate, isopropalin, isoxaben, isoxachlortole, isoxaflutole, isoxapyrifop, karbutilate, ketospiradox, lactofen, MAA, MAMA, MCPA esters and amines, MCPA-thioethyl, MCPB, mecoprop, mecoprop-P, medinoterb, mefenacet, mefluidide, mesosulfuron, mesotrione, metam, metamifop, metazachlor, metflurazon, methalpropalin, methazole, methiobencarb, methiozolin, methyl bromide, methyl isothiocyanate, metolachlor, metosulam, molinate, monalide, monochloroacetic acid, morfamquat, MSMA, naproanilide, napropamide, napropamide-M, naptalam, nicosulfuron, nipyraclofen, nitralin, nitrofen, nitrofluorfen, norflurazon, OCH, orbencarb, ortho-dichlorobenzene, oryzalin, oxadiargyl, oxadiazon, oxapyrazon, oxasulfuron, oxaziclomefone, oxyfluorfen, paraflufen-ethyl, paraquat, pebulate, pelargonic acid, pendimethalin, pentachlorophenol, pentoxazone, perfluidone, pethoxamid, phenisopham, phenylmercury acetate, picloram, picolinafen, pinoxaden, piperophos, potassium arsenite, potassium azide, potassium cyanate, pretilachlor, primisulfuron-methyl, prodiamine, profluazol, profluralin, profoxydim, prohexadione-calcium, pronamide, propachlor, propaquizafop, propham, propisochlor, propoxycarbazone, propyzamide, prosulfalin, prosulfocarb, prosulfuron, proxan, prynachlor, pydanon, pyraflufen-ethyl, pyrasulfotole, pyrazogyl, pyrazolynate, pyrazoxyfen, pyributicarb, pyriclor, pyrithiobac-sodium, pyroxasulfone, quinclorac, quinmerac, quinoclamine, quinonamid, quizalofop, quizalofop-P-ethyl, rhodethanil, rimsulfuron, saflufenacil, S-metolachlor, sethoxydim, siduron, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tefuryltrione, tembotrione, tepraloxydim, terbucarb, terbuchlor, thenylchlor, thiameturon, thiazopyr, thidiazimin, thiencarbazone-methyl, thifensulfuron, thifensulfuron-methyl, thiobencarb, tiafenacil, tiocarbazil, tioclorim, tolpyralate, topramezone, tralkoxydim, triallate, triafamone, triasulfuron, tribenuron, tribenuron-methyl, tricamba, triclopyr choline salt, triclopyr esters and amines, tridiphane, trifloxysulfuron, trifluralin, triflusulfuron, trifop, trifopsime, trimeturon, tripropindan, tritac, tritosulfuron, vernolate, xylachlor and salts, esters, optically active isomers, and mixtures thereof.

In some embodiments, the additional pesticide or an agriculturally acceptable salt or ester thereof is provided in a premixed formulation with (a), (b), or combinations thereof. In some embodiments, the pyridine carboxylic acid herbicide or an agriculturally acceptable N-oxide, salt, or ester thereof is provided in a premixed formulation with an additional pesticide. In some embodiments, the photosystem II inhibitor or an agriculturally acceptable salt or ester thereof is provided in a premixed formulation with an additional pesticide.

In some embodiments, the photosystem II inhibitor is bromoxynil or an agriculturally acceptable salt or ester thereof, and the bromoxynil or an agriculturally acceptable salt or ester thereof is provided in a premixed formulation with an additional pesticide. Exemplary premixes of bromoxynil or an agriculturally acceptable salt or ester thereof and additional pesticides include commercially available premixes of bromoxynil or an agriculturally acceptable salt or ester thereof with additional pesticides including atrazine, benazolin, bentazone, 2,4-D, dicamba, ethofumesate, fenoxaprop-P-ethyl, fluroxypyr, ioxynil, isoproturon, MCPA, mecoprop, mecoprop-P, propanil, pyrasulfotole, terbuthylazine, and thiencarbazone-methyl.

In some embodiments, the photosystem II inhibitor is bentazon or an agriculturally acceptable salt thereof, and the bentazon or an agriculturally acceptable salt thereof is provided in a premixed formulation with an additional pesticide. Exemplary premixes of bentazon or an agriculturally acceptable salt thereof and additional pesticides include commercially available premixes of bentazon or an agriculturally acceptable salt thereof with additional pesticides including acifluorfen-sodium, atrazine, bifenox, bromoxynil, cyhalofop-butyl, dicamba-sodium, dichlorprop-potassium, fomesafen, imazethapyr-ammonium, MCPA-acid, MCPA-sodium, MCPB-sodium, pendimethalin, paraquat dichloride, sethoxydim, and terbuthylazine.

In some embodiments, the photosystem II inhibitor is isoproturon, and the isoproturon is provided in a premixed formulation with an additional pesticide. Exemplary premixes of isoproturon and additional pesticides include commercially available premixes of isoproturon with additional pesticides including amidosulfuron, beflubutamid, bifenox, carfentrazone-ethyl, chlorotoluron diflufenican, fenoxaprop-P-ethyl, pendimethalin, picolinafen, and simazine.

In some embodiments, the photosystem II inhibitor is metribuzin or an agriculturally acceptable salt thereof, and the metribuzin or an agriculturally acceptable salt thereof is provided in a premixed formulation with an additional pesticide. Exemplary premixes of metribuzin or an agriculturally acceptable salt thereof and additional pesticides include commercially available premixes of metribuzin or an agriculturally acceptable salt thereof with additional pesticides including 2,4-D, chlorimuron-ethyl, flufenacet, S-metolachlor, rimsulfuron, and sulfentrazone.

In some embodiments, the photosystem II inhibitor is atrazine or an agriculturally acceptable salt thereof, and the atrazine or an agriculturally acceptable salt thereof is provided in a premixed formulation with an additional pesticide. Exemplary premixes of atrazine or an agriculturally acceptable salt thereof and additional pesticides include commercially available premixes of atrazine or an agriculturally acceptable salt thereof with additional pesticides including acetochlor, benoxacor, dicamba-potassium, dichlormid, mesotrione, S-metolachlor, and terbutryn.

D. Adjuvants/Carriers/Colorants/Adhesives

In some embodiments, the additive includes an agriculturally acceptable adjuvant.

Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, herbicide safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphate alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8 EO); tallow amine ethoxylate (15 EO); and PEG(400) dioleate-99.

In some embodiments, the additive is a safener, which is an organic compound leading to better crop plant compatibility when applied with a herbicide. In some embodiments, the safener itself is herbicidally active. In some embodiments, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, R29148, and N-phenylsulfonylbenzoic acid amides, as well as thereof agriculturally acceptable salts and, provided they have a carboxyl group, their agriculturally acceptable derivatives. In some embodiments, the safener can be cloquintocet or an ester or salt or ester thereof, such as cloquintocet (mexyl). In some embodiments, the safener can be dichlormid.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivatives, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes, or oil dispersions can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) and optionally a safener with a solid carrier.

In some embodiments, granules (e.g., coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In formulations designed to be employed as concentrates, (a) and (b) can be present in a concentration of from 0.1 to 98 weight percent (0.5 to 90 weight percent), based on the total weight of the formulation. Concentrates can be diluted with an inert carrier, such as water, prior to application. The diluted formulations applied to undesired vegetation or the locus of undesired vegetation can contain from 0.0006 to 8.0 weight percent of (a) and (b) (e.g., from 0.001 to 5.0 weight percent), based on the total weight of the diluted formulation.

In some embodiments, (a) and (b), independently, can be employed in a purity of from 90% to 100% (e.g., from 95% to 100%) according to nuclear magnetic resonance (NMR) spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to NMR spectrometry.

III. Methods of Use

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

The compositions disclosed herein can be applied pre-emergence (before the emergence of undesirable vegetation) or post-emergence (i.e., during and/or after emergence of the undesirable vegetation). If desired, the compositions can be applied as an in-water application. In some embodiments, the pyridine carboxylic acid herbicide or an agriculturally acceptable N-oxide, salt, or ester thereof and the photosystem II inhibitor or an agriculturally acceptable salt or ester thereof are applied simultaneously.

When the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applied to soil or water to prevent the emergence or growth of vegetation by spraying (e.g., foliar spraying). In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some embodiments, the compositions disclosed herein are applied by the low-volume or the ultra-low-volume method, wherein the application is in the form of micro granules. In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or the bare soil (e.g., post-directed or lay-by). In some embodiments, the compositions disclosed herein can be applied as dry formulations (e.g., granules, WDGs, etc.) into water.

In some embodiments, herbicidal activity is exhibited by the compounds of the mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action. In some cases, the compositions are applied to relatively immature undesirable vegetation.

The compositions and methods disclosed herein can be used to control undesired vegetation in a variety of crop and non-crop applications. In some embodiments, the compositions and methods disclosed herein can be used for controlling undesired vegetation in crops. In some embodiments, the undesirable vegetation is controlled in a row crop. Exemplary crops include, but are not limited to, wheat, barley, triticale, rye, teff, oats, corn/maize, cotton, soy, *sorghum*, rice, sugarcane and rangeland (e.g., pasture grasses). In some embodiments, the compositions and methods disclosed herein can be used for controlling undesired vegetation in corn/maize, wheat (e.g., spring wheat, winter wheat, durum wheat), or a combination thereof.

The compositions and methods disclosed herein can be used for controlling undesired vegetation in non-crop areas. Exemplary non-crop areas include, but are not limited to, turfgrass, pastures, grasslands, fallow land, rights-of-way, aquatic settings, tree and vine, wildlife management areas, or rangeland. In some embodiments, the compositions and methods disclosed herein can be used in industrial vegetation management (IVM) or for utility, pipeline, roadside, and railroad rights-of-way applications. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program lands (CRP), trees, vines, grasslands, and grasses grown for seeds. In some embodiments, the compositions and methods disclosed herein can be used on lawns (e.g., residential, industrial, and institutional), golf courses, parks, cemeteries, athletic fields, and sod farms.

The compositions and methods disclosed herein can also be used in crop plants that are resistant to, for instance, herbicides, pathogens, and/or insects. In some embodiments, the compositions and methods disclosed herein can be used in crop plants that are resistant to one or more herbicides because of genetic engineering or breeding. In some embodiments, the compositions and methods disclosed herein can be used in crop plants that are resistant to one or more pathogens such as plant pathogenous fungi owing to genetic engineering or breeding. In some embodiments, the compositions and methods disclosed herein can be used in crop plants that are resistant to attack by insects owing to genetic engineering or breeding. Exemplary resistant crops include, but are not limited to, crops that owing to introduction of the gene for *Bacillus thuringiensis* (or Bt) toxin by genetic modification, are resistant to attack by certain insects. In some embodiments, the compositions and methods described herein can be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, and protoporphyrinogen oxidase (PPO) inhibitors to control vegetation in crops tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, or combinations thereof. In some embodiments, the undesirable vegetation is controlled in glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, and protoporphyrinogen oxidase (PPO) inhibitors tolerant crops possessing single, multiple or stacked traits conferring tolerance to single or multiple chemistries and/or multiple modes of action. In some embodiments, the undesirable vegetation can be controlled in a crop that is ACCase-tolerant, ALS-tolerant, or a combination thereof. The combination of (a), (b), and a complementary herbicide or salt or ester thereof can be used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix, or as sequential applications.

The compositions and methods may be used in controlling undesirable vegetation in crops possessing agronomic stress tolerance (including but not limited to drought, cold, heat, salt, water, nutrient, fertility, pH), pest tolerance (including but not limited to insects, fungi and pathogens) and crop improvement traits (including but not limited to yield; protein, carbohydrate, or oil content; protein, carbohydrate, or oil composition; plant stature and plant architecture).

In some embodiments, the compositions disclosed herein can be used for controlling undesirable vegetation including grasses, broadleaf weeds, sedge weeds, and combinations thereof. In some embodiments, the compositions disclosed herein can be used for controlling undesirable vegetation including, but not limited to, *Polygonum* species such as wild buckwheat (*Polygonum convolvulus*), *Amaranthus* species such as pigweed (*Amaranthus retroflexus*), *Chenopodium* species such as common lambsquarters (*Chenopodium album* L.), *Sida* species such as prickly *sida* (*Sida spinosa* L.), *Ambrosia* species such as common ragweed (*Ambrosia artemisiifolia*), *Cyperus* species such as nutsedge (*Cyperus esculentus*), *Setaria* species such as giant foxtail (*Setaria faberi*), *Sorghum* species, *Acanthospermum* species, *Anthemis* species, *Atriplex* species, *Brassica* species, *Cirsium* species, *Convolvulus* species, *Conyza* species, such as horseweed (*Conyza canadensis*), *Cassia* species, *Commelina* species, *Datura* species, *Digitaria* species, *Echinochloa* species, *Euphorbia* species, *Geranium* species, *Galinsoga* species, *Ipomoea* species such as morning-glory, *Lamium* species, *Malva* species, *Matricaria* species, *Persicaria* species, *Prosopis* species, *Rumex* species, *Sisymbrium* species, *Solanum* species, *Trifolium* species, *Xanthium* species, *Veronica* species, *Viola* species such as wild pansy (*Viola tricolor*), common chickweed (*Stellaria media*), velvetleaf (*Abutilon theophrasti*), hemp *sesbania* (*Sesbania exaltata* Cory), *Anoda cristata*, *Bidens pilosa*, *Brassica kaber*, shepherd's purse (*Capsella bursa-pastoris*), cornflower (*Centaurea cyanus* or *Cyanus segetum*), hempnettle (*Galeopsis tetrahit*), cleavers (*Galium aparine*), common sunflower (*Helianthus annuus*), *Desmodium tortuosum*, kochia (*Kochia scoparia*), *Medicago arabica*, *Mercurialis annua*, *Myosotis arvensis*, common poppy (*Papaver rhoeas*), *Raphanus raphanistrum*, Russian thistle (*Salsola kali*), wild mustard (*Sinapis arvensis*), *Sonchus arvensis*, *Thlaspi arvense*, *Tagetes minuta*, *Richardia brasiliensis*, *Plantago major*, *Plantago lanceolata*, bird's-eye speedwell (*Veronica persica*) and speedwell.

In certain embodiments, the undesirable vegetation includes velvetleaf (ABUTH, *Abutilon theophrasti*), pigweed (AMARE, *Amaranthus retroflexus*), rape (BRSNN, *Brassica napus*), thistle (CIRAR, *Cirsium arvense*), nutsedge (CYPES, *Cyperus esculentus*), large crabgrass (DIGSA, *Digitaria sanguinalis*), barnyardgrass (ECHCG, *Echinochloa crus-galli*), poinsettia (EPHHL, *Euphorbia heterophylla*), common sunflower (HELAN, *Helianthus annuus*), ivyleaf morningglory (IPOHE, *Ipomoea hederacea*), ivy-leaved speedwell (VERHE, *Veronica hederifolia*), wild pansy (VIOTR, *Viola tricolor*), or a combination thereof.

In certain embodiments, the undesirable vegetation includes pigweed (AMARE, *Amaranthus retroflexus*), poinsettia (*Euphorbia heterophylla*, EPHHL), nutsedge (*Cyperus esculentus*, CYPES), morning glory (*Ipomoea hederacea*, IPOHE), or a combination thereof.

The herbicidal compositions described herein can be used to control herbicide resistant or tolerant weeds. The methods employing the compositions described herein may also be employed to control herbicide resistant or tolerant weeds. Exemplary resistant or tolerant weeds include, but are not limited to, biotypes resistant or tolerant to acetolactate synthase (ALS) or acetohydroxy acid synthase (AHAS) inhibitors (e.g., imidazolinones, sulfonylureas, pyrimidinylthiobenzoates, triazolopyrimidines, sulfonylaminocarbonyltriazolinones), acetyl CoA carboxylase (ACCase) inhibitors (e.g., aryloxyphenoxypropionates, cyclohexanediones, phenylpyrazolines), synthetic auxins (e.g., benzoic acids, phenoxycarboxylic acids, pyridine carboxylic acids, quinoline carboxylic acids), auxin transport inhibitors (e.g., phthalamates, semicarbazones), photosystem I inhibitors (e.g., bipyridyliums), 5-enolpyruvylshikimate-3-phosphate (EPSP) synthase inhibitors (e.g., glyphosate), glutamine synthetase inhibitors (e.g., glufosinate, bialafos), microtubule assembly inhibitors (e.g., benzamides, benzoic acids, dinitroanilines, phosphoramidates, pyridines), mitosis inhibitors (e.g., carbamates), very long chain fatty acid (VLCFA) inhibitors (e.g., acetamides, chloroacetamides, oxyacetamides, tetrazolinones), fatty acid and lipid synthesis inhibitors (e.g., phosphorodithioates, thiocarbamates, benzofuranes, chlorocarbonic acids), protoporphyrinogen oxidase (PPO) inhibitors (e.g., diphenylethers, N-phenylphthalimides, oxadiazoles, oxazolidinediones, phenylpyrazoles, pyrimidinediones, thiadiazoles, triazolinones), carotenoid biosynthesis inhibitors (e.g., clomazone, amitrole, aclonifen), phytoene desaturase (PDS) inhibitors (e.g., amides, anilidex, furanones, phenoxybutan-amides, pyridiazinones, pyridines), 4-hydroxyphenyl-pyruvate-dioxygenase (HPPD) inhibitors (e.g., callistemones, isoxazoles, pyrazoles, triketones), cellulose biosynthesis inhibitors (e.g., nitriles, benzamides, quinclorac, triazolocarboxamides), herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, biotypes with resistance or tolerance to multiple chemical classes, biotypes with resistance or tolerance to multiple herbicide modes-of-action, and biotypes with multiple resistance or tolerance mechanisms (e.g., target site resistance or metabolic resistance).

By way of non-limiting illustration, examples of certain embodiments of the present disclosure are given below.

EXAMPLES

Example 1. Herbicidal Activity and Effect on Crop Injury on Winter Wheat of Compounds of Formula (I) and Photosystem II in Greenhouse Trials Methodology—Evaluation of Postemergence Herbicidal Activity in Crops Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical or formulated material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Stocks solutions of the safeners were prepared following the same procedure. Spray solutions of the compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank. Application rates of component (a) are in g ae/ha and application rates of component (b) are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

Compound 7 was formulated as a soluble concentrate (SL) and was combined with bromoxynil and applied to winter wheat (TRZAW) and spring barley (HORVS) and the phytotoxicity of the herbicidal composition was measured. In addition, the efficacy of the herbicidal composition on pigweed (AMARE, *Amaranthus retroflexus*) and thistle (CIRAR, *Cirsium arvense*) was evaluated. The results are summarized in Tables 1 and 2.

TABLE 1

Effect (% visual injury) of compound 7 and bromoxynil on cereal weeds.

| Application Rate | Compound 7 (g ae/ha) | 8.75 | 0 | 8.75 |
|---|---|---|---|---|
| | Bromoxynil (g ai/ha) | 0 | 140 | 140 |
| AMARE | Obs | 70 | 0 | 84 |
| | Exp | — | — | 70 |
| | Δ | | | 14 |
| TRZAW | Obs | 0 | 0 | 0 |
| | Exp | — | — | 0 |
| | Δ | | | 0 | g ae/ha = grams acid equivalent per hectare
g ai/ha = grams active ingredient per hectare
AMARE = *Amaranthus retroflexus* (pigweed)
TRZAW = *Triticum aestivum* (winter wheat)

TABLE 2

Effect (% visual injury) of compound 7 and bromoxynil on cereal weeds.

| Application Rate | Compound 7 (g ae/ha) | 5 | 10 | 0 | 5 | 10 |
|---|---|---|---|---|---|---|
| | Bromoxynil (g ai/ha) | 0 | 0 | 70 | 70 | 70 |
| CIRAR | Obs | 50 | 65 | 40 | 97 | 93 |

TABLE 2-continued

Effect (% visual injury) of compound 7 and bromoxynil on cereal weeds.

|  |  |  |  |  |  |  |
|---|---|---|---|---|---|---|
|  | Exp | — | — | — | 70 | 79 |
|  | Δ |  |  |  | 27 | 14 |
| HORVS | Obs | 0 | 15 | 0 | 0 | 10 |
|  | Exp | — | — | — | 0 | 15 |
|  | Δ |  |  |  | 0 | −5 |
| TRZAW | Obs | 10 | 20 | 0 | 10 | 20 |
|  | Exp | — | — | — | 10 | 20 |
|  | Δ |  |  |  | 0 | 0 | g ae/ha = grams acid equivalent per hectare
g ai/ha = grams active ingredient per hectare
CIRAR = *Cirsium arvense* (thistle)
HORVS = *Hordeum vulgare* (spring barley)
TRZAW = *Tritium aestivum* (winter wheat)

Example 2. Herbicidal Activity and Effect on Crop Injury on Winter Wheat and Corn/Maize of Compounds of Formula (I) and Photosystem II Inhibitors in Greenhouse Trials Methodology—Evaluation of Postemergence Herbicidal Activity in Crops Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical or formulated material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Stocks solutions of the compound mixtures were prepared following the same procedure. Spray solutions of the safeners and experimental compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank. Application rates of component (a) are in g ae/ha and application rates of component (b) are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

Compound 2 was formulated as an emulsifiable concentrate (EC) and was combined with bromoxynil and applied to winter wheat (TRZAW) and maize (ZEAMX) and the phytotoxicity of the herbicidal composition was measured. In addition, the efficacy of the herbicidal composition on pigweed (AMARE, *Amaranthus retroflexus*), poinsettia (*Euphorbia heterophylla*, EPHHL), nutsedge (*Cyperus esculentus*, CYPES), and ivyleaf morningglory (*Ipomoea hederacea*, IPOHE) was evaluated. The results are summarized in Table 3.

TABLE 3

Effect (% visual injury) of compound 2 and bromoxynil on weeds.

| Application Rate | Compound 2 (g ae/ha) | 5 | 10 | 0 | 5 | 10 |
|---|---|---|---|---|---|---|
|  | Bromoxynil (g ai/ha) | 0 | 0 | 70 | 70 | 70 |
| AMARE | Obs | 88 | 100 | 20 | 95 | 98 |
|  | Exp | — | — | — | 90 | 100 |
|  | Δ |  |  |  | 5 | −3 |
| EPHHL | Obs | 35 | 75 | 5 | 75 | 100 |
|  | Exp | — | — | — | 38 | 76 |
|  | Δ |  |  |  | 37 | 24 |
| CYPES | Obs | 5 | 10 | 0 | 23 | 28 |
|  | Exp | — | — | — | 5 | 10 |
|  | Δ |  |  |  | 18 | 18 |
| IPOHE | Obs | 10 | 20 | 25 | 65 | 60 |
|  | Exp | — | — | — | 33 | 40 |
|  | Δ |  |  |  | 33 | 20 |
| ZEAMX | Obs | 3 | 3 | 0 | 0 | 0 |
|  | Exp | — | — | — | 3 | 3 |
|  | Δ |  |  |  | −3 | −3 |
| TRZAW | Obs | 3 | 3 | 0 | 0 | 3 |
|  | Exp | — | — | — | 3 | 3 |
|  | Δ |  |  |  | −3 | 0 | g ae/ha = grams acid equivalent per hectare
g ai/ha = grams active ingredient per hectare
AMARE = *Amaranthus retroflexus* (pigweed)
EPHHL = *Euphorbia heterophylla* (poinsettia)
CYPES = *Cyperus esculentus* (nutsedge)
IPOHE = *Ipomoea hederacea* (ivyleaf morningglory)
ZEAMX = *Zea mays* (maize)
TRZAW = *Triticum aestivum* (winter wheat)

Example 3. Herbicidal Activity and Effect on Crop Injury on Winter Wheat and Corn of Compounds of Formula (I) and Photosystem II Inhibitors in Greenhouse Trials Methodology—Evaluation of Postemergence Herbicidal Activity in Crops Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photoperiod which was maintained at about 23° C. during the day and 22° C. during the night. Nutrients and water were added on a regular basis and supplemental lighting was provided with overhead metal halide 1000-Watt lamps as necessary. The plants were employed for testing when they reached the second or third true leaf stage.

Weighed amounts of technical or formulated material were dissolved in a volume of 97:3 volume per volume (v/v) acetone/dimethyl sulfoxide (DMSO) to stock solutions. If the experimental compound did not dissolve readily, the mixture was warmed and/or sonicated. The concentrated stock solutions were diluted with an aqueous mixture of 1.5% v/v of Agri-dex crop oil concentrate to provide the appropriate application rates. Compound requirements are based upon a 12 milliliter (mL) application volume at a rate of 187 liters per hectare (L/ha). Stocks solutions of the safeners were prepared following the same procedure. Spray solutions of the compound mixtures were prepared by adding the stock solutions to the appropriate amount of dilution solution to form a 12 mL spray solution in two-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank. Application rates of component (a) are in g ae/ha and application rates of component (b) are in g ai/ha.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill. The condition of the test plants was compared with that of the control plants as determined visually and scored on a scale of 0 to 100 percent, where 0 corresponds to no injury and 100 corresponds to complete kill. Colby's equation was used to determine the herbicidal effects expected from the mixtures.

Compound 1 was formulated as an EC and combined with bentazon, isoproturon, metribuzin and atrazine. The mixtures were applied to winter wheat (TRZAW) and corn (ZEAMX), and rice (ORYSA), and the phytotoxicity of the herbicidal composition was measured. In addition, the efficacy of the herbicidal composition on velvetleaf (*Abutilon theophrasti*, ABUTH), pigweed (*Amaranthus retroflexus*, AMARE), rape (*Brassica napus*, BRSNN), lambsquarters (*Chenopodium album*, CHEAL), thistle (*Cirsium arvense*, CIRAR), nutsedge (*Cyperus esculentus*, CYPES), large crabgrass (*Digitaria sanguinalis*, DIGSA), barnyardgrass (*Echinochloa crus-galli*, ECHCG), poinsettia (*Euphorbia heterophylla*, EPHHL), common sunflower (*Helianthus annuus*, HELAN), ivyleaf morningglory (*Ipomoea hederacea*, IPOHE), ivy-leaved speedwell (VERHE, *Veronica hederifolia*), and wild pansy (VIOTR, *Viola tricolor*) was evaluated. The condition of the test plants as compared with that of the control plants was determined visually and scored on a scale of 0 to 100 percent where 0 corresponds to no injury and 100 corresponds to complete kill. Colby's equation was used to determine the herbicidal effects expected from the mixtures. The results are summarized in Tables 4-7.

TABLE 4

Effect (%visual injury) of compound 1 and bentazon on weeds.

| Application Rate | Compound 1 (g ae/ha) | 5 | 0 | 5 |
|---|---|---|---|---|
|  | Bentazon (g ai/ha) | 0 | 60 | 60 |
| ABUTH | Obs | 10 | 0 | 70 |
|  | Exp |  |  | 10 |
|  | Δ |  |  | 60 |
| AMARE | Obs | 93 | 10 | 100 |
|  | Exp |  |  | 94 |
|  | Δ |  |  | 6 |
| BRSNN | Obs | 50 | 20 | 85 |
|  | Exp |  |  | 60 |
|  | Δ |  |  | 25 |
| CIRAR | Obs | 20 | 0 | 50 |
|  | Exp |  |  | 20 |
|  | Δ |  |  | 30 |
| CYPES | Obs | 10 | 0 | 65 |
|  | Exp |  |  | 10 |
|  | Δ |  |  | 55 |
| DIGSA | Obs | 0 | 0 | 10 |
|  | Exp |  |  | 0 |
|  | Δ |  |  | 10 |
| ECHCG | Obs | 60 | 0 | 80 |
|  | Exp |  |  | 60 |
|  | Δ |  |  | 20 |
| EPHHL | Obs | 97 | 0 | 100 |
|  | Exp |  |  | 97 |
|  | Δ |  |  | 3 |
| TRZAW | Obs | 10 | 0 | 0 |
|  | Exp |  |  | 10 |
|  | Δ |  |  | -10 |
| ZEAMX | Obs | 10 | 0 | 0 |
|  | Exp |  |  | 10 |
|  | Δ |  |  | -10 | g ae/ha = grams acid equivalent per hectare
g ai/ha = grams active ingredient per hectare
ABUTH = *Abutilon theophrasti* (velvetleaf)
AMARE = *Amaranthus retroflexus* (pigweed)
BRSNN = *Brassica napus* (rape)
CIRAR = *Cirsium arvense* (thistle)
CYPES = *Cyperus esculentus* (nutsedge)
DIGSA = *Digitaria sanguinalis* (large crabgrass)
ECHCG = *Echinochloa crus-galli* (barnyardgrass)
EPHHL = *Euphorbia heterophylla* (poinsettia)
TRZAW = *Triticum aestivum* (winter wheat);
ZEAMX = *Zea mays* (corn)

TABLE 5

Effect (%visual injury) of compound 1 and isoproturon on weeds.

| Application Rate | Compound 1 (g ae/ha) | 5 | 0 | 5 |
|---|---|---|---|---|
|  | Isoproturon (g ai/ha) | 0 | 150 | 150 |
| BRSNN | Obs | 50 | 0 | 80 |
|  | Exp |  |  | 50 |
|  | Δ |  |  | 30 |
| CIRAR | Obs | 20 | 10 | 70 |
|  | Exp |  |  | 28 |
|  | Δ |  |  | 42 |
| CYPES | Obs | 10 | 0 | 30 |
|  | Exp |  |  | 10 |
|  | Δ |  |  | 20 |

TABLE 5-continued

Effect (%visual injury) of compound 1 and isoproturon on weeds.

| | | | | |
|---|---|---|---|---|
| ECHCG | Obs | 60 | 0 | 100 |
| | Exp | | | 60 |
| | Δ | | | 40 |
| HELAN | Obs | 97 | 0 | 100 |
| | Exp | | | 97 |
| | Δ | | | 3 |
| VIOTR | Obs | 10 | 0 | 20 |
| | Exp | | | 10 |
| | Δ | | | 10 |
| TRZAW | Obs | 10 | 0 | 0 |
| | Exp | | | 10 |
| | Δ | | | -10 |
| ZEAMX | Obs | 10 | 0 | 0 |
| | Exp | | | 10 |
| | Δ | | | -10 | g ae/ha = grams acid equivalents per hectare
g ai/ha = grams active ingredient per hectare
BRSNN = *Brassica napus* (rape)
CIRAR = *Cirsium arvense* (thistle)
CYPES = *Cyperus esculentus* (nutsedge)
ECHCG = *Echinochloa crus-galli* (barnyardgrass)
HELAN = *Helianthus annuus* (common sunflower)
VIOTR = *Viola tricolor* (Wild pansy)
TRZAW = *Triticum aestivum* (winter wheat)
ZEAMX = *Zea mays* (corn)

TABLE 6

Effect (%visual injury) of compound 1 and metribuzin on weeds.

| Application Rate | Compound 1 (g ae/ha)<br>Metribuzin (g ai/ha) | 5<br>0 | 0<br>25 | 5<br>25 |
|---|---|---|---|---|
| AMARE | Obs | 93 | 10 | 100 |
| | Exp | | | 94 |
| | Δ | | | 6 |
| BRSNN | Obs | 50 | 0 | 85 |
| | Exp | | | 50 |
| | Δ | | | 35 |
| CIRAR | Obs | 20 | 10 | 60 |
| | Exp | | | 28 |
| | Δ | | | 32 |
| CYPES | Obs | 10 | 0 | 80 |
| | Exp | | | 10 |
| | Δ | | | 70 |
| ECHCG | Obs | 60 | 0 | 97 |
| | Exp | | | 60 |
| | Δ | | | 37 |
| EPHHL | Obs | 97 | 0 | 100 |
| | Exp | | | 97 |
| | Δ | | | 3 |
| ORYSA | Obs | 0 | 0 | 10 |
| | Exp | | | 0 |
| | Δ | | | 10 |
| TRZAW | Obs | 10 | 0 | 0 |
| | Exp | | | 10 |
| | Δ | | | -10 |
| ZEAMX | Obs | 10 | 0 | 0 |
| | Exp | | | 10 |
| | Δ | | | -10 | g ae/ha = grams acid equivalent per hectare
g ai/ha = grams active ingredient per hectare
AMARE = *Amaranthus retroflexus* (pigweed)
BRSNN = *Brassica napus* (rape)
CIRAR = *Cirsium arvense* (thistle)
CYPES = *Cyperus esculentus* (nutsedge)
ECHCG = *Echinochloa crus-galli* (barnyardgrass)
EPHHL = *Euphorbia heterophylla* (poinsettia)
ORYSA = *Oryza sativa* (common rice)
TRZAW = *Triticum aestivum* (winter wheat)
ZEAMX = *Zea mays* (corn)

TABLE 7

Effect (% visual injury) of compound 1 and atrazine on weeds.

| Application Rate | Compound 1 (g ae/ha)<br>Atrazine (g ai/ha) | 5<br>0 | 0<br>450 | 5<br>450 |
|---|---|---|---|---|
| AMARE | Obs | 65 | 50 | 93 |
| | Exp | | | 83 |
| | Δ | | | 11 |
| EPHHL | Obs | 97 | 0 | 100 |
| | Exp | | | 97 |
| | Δ | | | 3 |
| VERHE | Obs | 40 | 45 | 70 |
| | Exp | | | 67 |
| | Δ | | | 3 |
| VIOTR | Obs | 5 | 5 | 20 |
| | Exp | | | 10 |
| | Δ | | | 10 | g ae/ha = grams acid equivalents per hectare
g ai/ha = grams active ingredient per hectare
AMARE = *Amaranthus retroflexus* (pigweed)
EPHHL = *Euphorbia heterophylla* (poinsettia)
VERHE = *Veronica hederifolia* (ivy-leaved speedwell)
VIOTR = *Viola tricolor* (wild pansy)

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A herbicidal composition comprising a herbicidally effective amount of
   (a) a pyridine carboxylic acid herbicide or an agriculturally acceptable N-oxide, salt, or ester thereof, and
   (b) a photosystem II inhibitor selected from the group consisting of bromoxynil, bentazon, isoproturon, metribuzin, atrazine, agriculturally acceptable salts and esters thereof, and combinations thereof,
   wherein (a) and (b) are provided in a weight ratio of (a) in grams acid equivalent to (b) in grams active ingredient of from 1:90 to 1:5, and wherein the pyridine carboxylic acid herbicide comprises a compound defined by the formula below

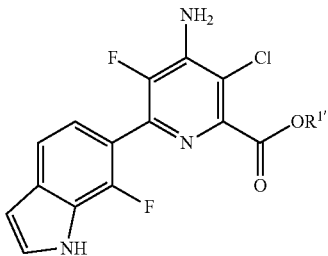

wherein $R^{1'}$ is hydrogen, or substituted or unsubstituted $C_7$-$C_{10}$ arylalkyl;

or an agriculturally acceptable N-oxide or salt thereof.

2. The composition of claim 1, wherein the pyridine carboxylic acid herbicide comprises one of the following:

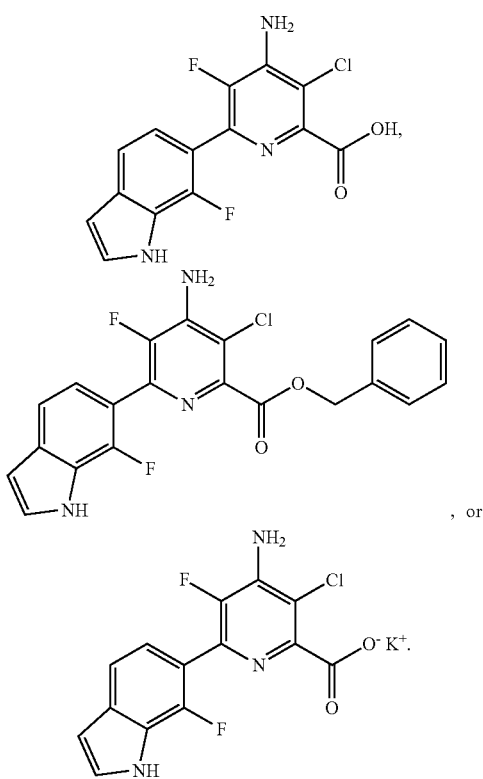

3. The composition of claim 1, wherein the pyridine carboxylic acid herbicide comprises

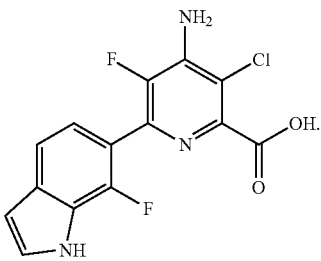 [SMILES: Nc1c(F)c(-c2ccc3cc[nH]c3c2F)nc(C(=O)O)c1Cl]

4. The composition of claim 1, wherein (b) is bromoxynil or an agriculturally acceptable salt or ester thereof.

5. The composition of claim 1, wherein (b) is isoproturon.

6. The composition of claim 1, wherein (b) is metribuzin or an agriculturally acceptable salt thereof.

7. The composition of claim 1, further comprising an agriculturally acceptable adjuvant or carrier.

8. The composition of claim 1, further comprising an additional pesticide.

9. The composition of claim 1, wherein the active ingredients in the composition consist of (a) and (b).

10. The composition of claim 1, which wherein the composition is provided as a herbicidal concentrate.

11. The composition of claim 1, wherein $R^{1'}$ is hydrogen.

12. The composition of claim 1, wherein $R^{1'}$ is a substituted or unsubstituted $C_8$ arylalkyl group.

13. The composition of claim 1, wherein $R^{1'}$ is a benzyl group.

14. A method of controlling undesirable vegetation comprising applying to vegetation or an area adjacent the vegetation or applying to soil or water to control the emergence or growth of vegetation a herbicidally effective amount of the composition of claim 1.

15. The method of claim 14, wherein (a) and (b) are applied post-emergence to the undesirable vegetation.

16. The method of claim 14, wherein (a) is applied in amount of from 0.1 g ae/ha to 300 g ae/ha.

17. The method of claim 14, wherein (b) is applied in amount of from 5 g ai/ha to 4000 g ai/ha.

18. The method of claim 14, further comprising applying an additional pesticide.

19. The method of claim 14, wherein the undesirable vegetation includes a broadleaf weed.

20. The method of claim 14, wherein the undesirable vegetation comprises a herbicide resistant or tolerant weed.

21. The method of claim 14, wherein the undesirable vegetation includes velvetleaf, pigweed, rape, thistle, nutsedge, large crabgrass, barnyardgrass, poinsettia, common sunflower, ivyleaf morningglory, wild pansy, ivy-leaved speedwell, or a combination thereof.

22. The method of claim 14, wherein the active ingredients applied to the vegetation or an area adjacent the vegetation or applied to soil or water to control the emergence or growth of vegetation consist of (a) and (b).

* * * * *